(12) United States Patent
Luo et al.

(10) Patent No.: US 8,288,522 B2
(45) Date of Patent: Oct. 16, 2012

(54) DETECTION OF NUCLEIC ACIDS THROUGH AMPLIFICATION OF SURROGATE NUCLEIC ACIDS

(75) Inventors: Yuling Luo, San Ramon, CA (US); Son Bui, Milpitas, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 13/207,237

(22) Filed: Aug. 10, 2011

(65) Prior Publication Data

US 2012/0009577 A1   Jan. 12, 2012

Related U.S. Application Data

(62) Division of application No. 11/595,789, filed on Nov. 9, 2006, now Pat. No. 8,017,360.

(60) Provisional application No. 60/735,808, filed on Nov. 10, 2005.

(51) Int. Cl.
*C07H 21/04* (2006.01)
*C12Q 1/68* (2006.01)
*C12P 19/34* (2006.01)

(52) U.S. Cl. ............ 536/24.3; 536/24.33; 435/6.1; 435/6.11; 435/6.12; 435/91.2

(58) Field of Classification Search ............... None
See application file for complete search history.

(56) References Cited

U.S. PATENT DOCUMENTS

| | | | |
|---|---|---|---|
| 4,868,105 | A | 9/1989 | Urdea et al. |
| 5,093,232 | A | 3/1992 | Urdea et al. |
| 5,124,246 | A | 6/1992 | Urdea et al. |
| 5,635,352 | A | 6/1997 | Urdea et al. |
| 5,681,697 | A | 10/1997 | Urdea et al. |
| 5,681,702 | A | 10/1997 | Collins et al. |
| 5,691,146 | A | 11/1997 | Mayrand |
| 5,747,244 | A | 5/1998 | Sheridan et al. |
| 5,780,227 | A | 7/1998 | Sheridan et al. |
| 5,849,481 | A | 12/1998 | Urdea et al. |
| 5,866,336 | A | 2/1999 | Nazarenko et al. |
| 5,981,180 | A | 11/1999 | Chandler et al. |
| 6,001,983 | A | 12/1999 | Benner |
| 6,007,994 | A | 12/1999 | Ward et al. |
| 6,037,120 | A | 3/2000 | Benner |
| 6,140,496 | A | 10/2000 | Benner |
| 6,232,462 | B1 | 5/2001 | Collins et al. |
| 6,277,607 | B1 | 8/2001 | Tyagi et al. |
| 6,418,382 | B2 | 7/2002 | Rothberg et al. |
| 6,449,562 | B1 | 9/2002 | Chandler et al. |
| 6,673,914 | B1 | 1/2004 | Hoon |
| 6,838,243 | B2 | 1/2005 | Lai et al. |
| 2002/0034753 | A1 | 3/2002 | Yang et al. |
| 2002/0172950 | A1 | 11/2002 | Kenny et al. |
| 2002/0172953 | A1 | 11/2002 | Mirkin et al. |
| 2003/0211489 | A1 | 11/2003 | Shen et al. |
| 2004/0115686 | A1 | 6/2004 | Dolginov et al. |
| 2004/0248103 | A1* | 12/2004 | Feaver et al. ............. 435/6 |
| 2005/0037397 | A1 | 2/2005 | Mirkin et al. |
| 2005/0170370 | A1 | 8/2005 | Rabbani et al. |
| 2006/0172284 | A1 | 8/2006 | Zheng et al. |
| 2006/0263769 | A1 | 11/2006 | Luo et al. |
| 2006/0286583 | A1 | 12/2006 | Luo et al. |
| 2007/0015188 | A1 | 1/2007 | Luo et al. |
| 2007/0161015 | A1 | 7/2007 | Zheng et al. |
| 2008/0038725 | A1 | 2/2008 | Luo et al. |
| 2008/0050746 | A1 | 2/2008 | McMaster et al. |
| 2008/0176242 | A1 | 7/2008 | McMaster et al. |
| 2009/0081688 | A1 | 3/2009 | Luo et al. |

FOREIGN PATENT DOCUMENTS

| | | |
|---|---|---|
| EP | 1 428 892 A | 6/2004 |
| WO | WO 94/00598 A1 | 1/1994 |
| WO | WO 95/16055 A1 | 6/1995 |
| WO | WO 01/94632 A2 | 12/2001 |
| WO | WO 2007/001986 A2 | 1/2007 |

OTHER PUBLICATIONS

Baner et al. (1998) "Signal amplification of padlock probes by rolling circle replication," *Nucleic Acids Res.*, 26(22):5073-5078.
Blok and Kramer (1997) "Amplifiable hybridization probes containing a molecular switch," *Mol Cell Probes*, 11(13):187-194.
Borucki (2005) "Suspension microarray with dendrimer signal amplification allows direct and high-throughput subtyping of *Listeria monocytogenes* from genomic DNA," *Journal of Clinical Microbiology*, p. 3255-3259.
Bustin (2000) "Absolute quantification of mRNA using real-time reverse transcription polymerase chain reaction assays," *Journal of Molecular Endocrinology*, 252:169-193.
Bustin (2002) "Quantification of mRNA using real-time reverse transcription PCR (RT-PCR): Trends and problems," *J Mol Endocrinol*, 29:23-39.
Bustin and Nolan (2004) "Pitfalls of quantitative real-time reverse-transcription polymerase chain reaction," *J Biomol Tech*, 15:155-166.
Collins et al. (1997) "A branched DNA signal amplification assay for quantification of nucleic acid targets below 100 molecules/ml," *Nucleic Acids Research*, 25(15):2979-2984.
Flagella et al. (2006) "A multiplex branched DNA assay for parallel quantitative gene expression profiling," *Anal Biochem*, 352:50-60.
Fulton et al. (1997) "Advanced multiplexed analysis with the FlowMetrix™ system," *Clinical Chemistry*, 43:1749-1756.
Hatch et al. (1999) "Rolling circle amplification of DNA immobilized on solid surfaces and its application to multiplex mutation detection," *Genet Anal*, 15(2):35-40.
Higuchi et al. (1993) "Kinetic PCR analysis: Real-time monitoring of DNA amplification reactions," *Bio/technology*, 11(9):1026-1030.
Hsu et al. (2001) "Genotyping single-nucleotide polymorphisms by the invader assay with dual-color fluorescence polarization detection," *Clinical Chemistry*, 47(8):1373-1377.
Kellar and Iannone (2002) "Multiplexed microsphere-based flow cytometric assays," *Experimental Hematology*, 30:1227-1237.
Kern et al. (1996) "An enhanced-sensitivity branched-DNA assay for quantification of human immunodeficiency virus type 1 RNA in plasma," *J. Clin. Microbiol.*, 34(12):3196-3202.

(Continued)

*Primary Examiner* — Angela M Bertagna
(74) *Attorney, Agent, or Firm* — Quine Intellectual Property Law Group, P.C.; Monicia Elrod-Erickson

(57) ABSTRACT

Methods for detecting and optionally quantitating one or more target nucleic acids are provided, in which a surrogate nucleic acid is captured to each target nucleic acid, amplified, and detected. Compositions, kit, and systems related to the methods are also described.

16 Claims, 4 Drawing Sheets

OTHER PUBLICATIONS

Klein (2002) "Quantification using real-time PCR technology: Applications and limitations," *Trends in Molecular Medicine*, 8(6):257-260.

Mackay et al. (2002) "Real-time PCR in virology," *Nucleic Acids Res.*, 30(6):1292-1305.

Malygin et al. (1996) "Hybridization of two oligodeoxynucleotides to both strands of an RNA hairpin structure increases the efficiency of RNA-DNA duplex formation," *FEBS Letters*, 392:114-116.

Marras et al. (1999) "Multiplex detection of single-nucleotide variation using molecular beacons," *Genetic Analysis: Biomolecular Engineering*, 14(5-6):151-156.

Martel et al. (2002) "Multiplexed screening assay for mRNA combining nuclease protection with luminescent array detection," *Assay Drug Dev Technol.*, 1:61-71.

Mhlanga and Malmberg (2001) "Using molecular beacons to detect single-nucleotide polymorphisms with real-time PCR," *Methods*, 25(4):463-471.

Nallur et al. (2001) "Signal amplification by rolling circle amplification on DNA microarrays," *Nucleic Acids Res.*, 29(23):E118.

Nazarenko et al. (1997) "A closed tube format for amplification and detection of DNA based on energy transfer," *Nucl. Acids Res.*, 25(12):2516-2521.

Player et al. (2001) "Single-copy gene detection using branched DNA (bDNA) in-situ hybridization," *The Journal of Histochemistry and Cytochemistry*, 49(5):603-611.

Poddar (2000) "Symmetric vs. asymmetric PCR and molecular beacon probe in the detection of a target gene of adenovirus," *Molecular and Cellular Probes*, 14(1):25-32.

Santalucia Jr. (1998) "A unified view of polymer, dumbbell, and oligonucleotide DNA nearest-neighbor thermodynamics, " *PNAS*, 95:1460-1465.

Schweitzer & Kingsmore (2001) "Combining nucleic acid amplification and detection," *Curr. Op Biotechnol.*, 12(1):21-27.

Shah et al. (1994) "Novel, ultrasensitive, Q-beta, replicase-amplified hybridization assay for detection of *Chlamydia trachomatis*," *J. Clin. Microbiol.*, 32(11):2718-2724.

Shah et al. (1995) "Detection of *Mycobacterium tuberculosis* directly from spiked human sputum by Q-beta replicase-amplifiied assay," *J. Clin. Microbiol.*, 33(2):322-328.

Shah et al. (2003) "Ultra-sensitive and specific detection of porcine endogenous retrovirus (PERV) using a sequence-capture real-time PCR approach," *J. Virol.Meth.*, 109:209-216.

Stone et al. (1996) "Detection of rRNA from four respiratory pathogens using an automated Qβ replicase assay," *Mol. Cell. Probes*, 10:359-370.

Tyagi and Kramer (1996) "Molecular beacons: probes that fluoresce upon hybridization," *Nature Biotechnology*, 14:303-308.

Van Cleve et al. (1998) "Direct quantitation of HIV by flow cytometry using branched DNA signal amplification," *Molecular and Cellular Probes*, 12 (4): 243-247.

Yang et al. (2001) "Badge, Beads Array for the Detection of Gene Expression, a high-throughput diagnostic bioassay," *Genome Res.*, 11:1888-1898.

Zhang et al. (2005) "Small interfering RNA and gene expression analysis using a multiplex branched DNA assay without RNA purification," *J Biomol Screen*, 10(6):549-556.

\* cited by examiner

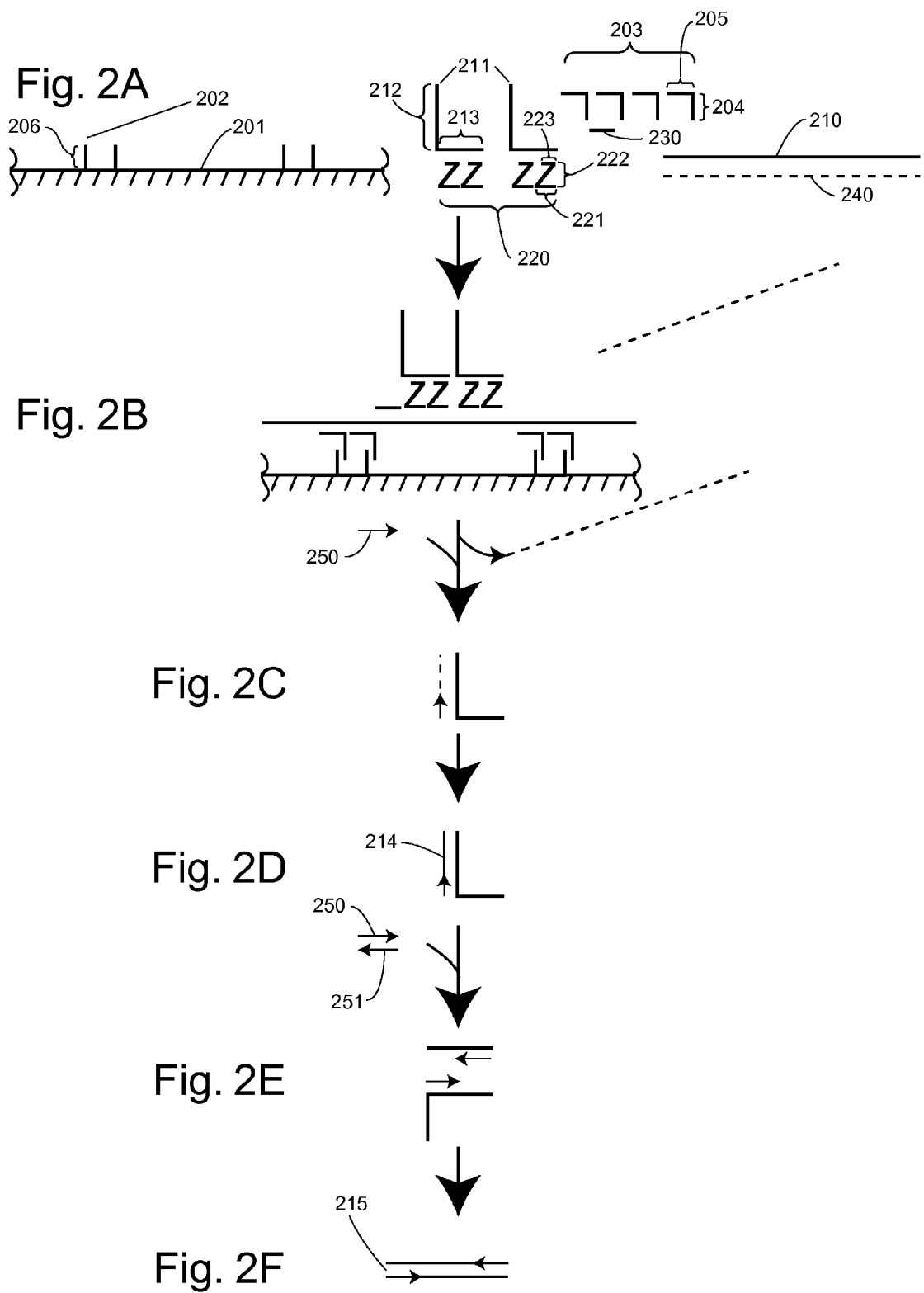

SEQUENCE LISTING

```
<160> NUMBER OF SEQ ID NOS: 40

<210> SEQ ID NO 1
<211> LENGTH: 120
<212> TYPE: DNA
<213> ORGANISM: Artificial
<220> FEATURE:
<223> OTHER INFORMATION: synthetic oligonucleotide probe

<400> SEQUENCE: 1
cgggtatggc tttcatgtgg ttctggacaa tgacggttac ggaggtgggc gtggtcgtct    60
gctgggttgg tcacgtgggc gatcgacttt ttaaaacggt aacttcatgc tttgactcag   120

<210> SEQ ID NO 2
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 2
cgggtatggc tttcatgtgg t                                               21

<210> SEQ ID NO 3
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 3
gtcgatcgcc cacgtgac                                                   18

<210> SEQ ID NO 4
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 4 tttttactt tctttccaag ag                                               22
```

<210> SEQ ID NO 5
<211> LENGTH: 55
<212> TYPE: DNA
<213> ORGANISM: Artificial
<220> FEATURE:
<223> OTHER INFORMATION: synthetic oligonucleotide probe

<400> SEQUENCE: 5
aagaggtgag tggctgtctg tgtttttctg agtcaaagca tgaagttacc gtttt    55

<210> SEQ ID NO 6
<211> LENGTH: 57
<212> TYPE: DNA
<213> ORGANISM: Artificial
<220> FEATURE:
<223> OTHER INFORMATION: synthetic oligonucleotide probe

<400> SEQUENCE: 6
gaatttgttt gtcaattcgt tctgttttc tgagtcaaag catgaagtta ccgtttt    57

<210> SEQ ID NO 7
<211> LENGTH: 60
<212> TYPE: DNA
<213> ORGANISM: Artificial
<220> FEATURE:
<223> OTHER INFORMATION: synthetic oligonucleotide probe

<400> SEQUENCE: 7
atctgttctg gaggtactct aggtatattt ttctgagtca aagcatgaag ttaccgtttt    60

<210> SEQ ID NO 8
<211> LENGTH: 56
<212> TYPE: DNA
<213> ORGANISM: Artificial
<220> FEATURE:
<223> OTHER INFORMATION: synthetic oligonucleotide probe

<400> SEQUENCE: 8
ggcttgttcc tcactactct caattttct gagtcaaagc atgaagttac cgtttt    56

<210> SEQ ID NO 9
<211> LENGTH: 54
<212> TYPE: DNA
<213> ORGANISM: Artificial
<220> FEATURE:
<223> OTHER INFORMATION: synthetic oligonucleotide probe

<400> SEQUENCE: 9
ctgcaggaac tggatcagga cttttctga gtcaaagcat gaagttaccg tttt    54

<210> SEQ ID NO 10
<211> LENGTH: 56
<212> TYPE: DNA
<213> ORGANISM: Artificial
<220> FEATURE:
<223> OTHER INFORMATION: synthetic oligonucleotide probe

<400> SEQUENCE: 10
gcatctagat tctttgcctt ttttttct gagtcaaagc atgaagttac cgtttt    56

<210> SEQ ID NO 11
<211> LENGTH: 52
<212> TYPE: DNA
<213> ORGANISM: Artificial
<220> FEATURE:
<223> OTHER INFORMATION: synthetic oligonucleotide probe

```
<400> SEQUENCE: 11
tgtgcctgca gcttcgtcat ttttctgagt caaagcatga agttaccgtt tt         52

<210> SEQ ID NO 12
<211> LENGTH: 53
<212> TYPE: DNA
<213> ORGANISM: Artificial
<220> FEATURE:
<223> OTHER INFORMATION: synthetic oligonucleotide probe

<400> SEQUENCE: 12
tgtcctgcag ccactggttc tttttctgag tcaaagcatg aagttaccgt ttt        53

<210> SEQ ID NO 13
<211> LENGTH: 57
<212> TYPE: DNA
<213> ORGANISM: Artificial
<220> FEATURE:
<223> OTHER INFORMATION: synthetic oligonucleotide probe

<400> SEQUENCE: 13
ggtttctgac cagaagaagg aatgtttttc tgagtcaaag catgaagtta ccgtttt    57

<210> SEQ ID NO 14
<211> LENGTH: 54
<212> TYPE: DNA
<213> ORGANISM: Artificial
<220> FEATURE:
<223> OTHER INFORMATION: synthetic oligonucleotide probe

<400> SEQUENCE: 14
aagttctgtg cccagtggac attttctga gtcaaagcat gaagttaccg tttt        54

<210> SEQ ID NO 15
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 15
tggggcaggg aaggca                                                 16

<210> SEQ ID NO 16
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 16
ggaatcttct cctgggggta c                                           21

<210> SEQ ID NO 17
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 17
tggggcggct acatcttt                                               18

<210> SEQ ID NO 18
<211> LENGTH: 27
<212> TYPE: DNA
```

```
<213> ORGANISM: Artificial
<220> FEATURE:
<223> OTHER INFORMATION: synthetic oligonucleotide probe

<400> SEQUENCE: 18
gctttcacac atgttactct tgttaca                                    27

<210> SEQ ID NO 19
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 19
tttggaaggt tcaggttgtt tt                                         22

<210> SEQ ID NO 20
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 20
cctcaaactc caaaagacca gtg                                        23

<210> SEQ ID NO 21
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 21
ttgggtcagg ggtggttatt                                            20

<210> SEQ ID NO 22
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 22
ctgcaggaac tccttaaagc tg                                         22

<210> SEQ ID NO 23
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 23
cccattaaca acaacaatct gagg                                       24

<210> SEQ ID NO 24
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 24
ggctcctgga ggcgagata                                             19
```

```
<210> SEQ ID NO 25
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 25
aactggaccg aaggcgct                                                 18

<210> SEQ ID NO 26
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 26
gcaggcaaca ccaggagc                                                 18

<210> SEQ ID NO 27
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 27
gatgccgtcg aggatgtacc                                               20

<210> SEQ ID NO 28
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 28
ctgccagtgc ctctttgct                                                19

<210> SEQ ID NO 29
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 29
gcatccatct ttttcagcca tc                                            22

<210> SEQ ID NO 30
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 30
atgattttca ccaggcaagt ct                                            22

<210> SEQ ID NO 31
<211> LENGTH: 24
<212> TYPE: DNA
<213> ORGANISM: Artificial
<220> FEATURE:
<223> OTHER INFORMATION: synthetic oligonucleotide probe
```

-continued

<400> SEQUENCE: 31
ttttgtactc atctgcacag ctct                                            24

<210> SEQ ID NO 32
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 32
gcaggctggc atttgtgg                                                   18

<210> SEQ ID NO 33
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 33
cgcagaatga gatgagttgt ca                                              22

<210> SEQ ID NO 34
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 34
tgcccatgct acatttgcc                                                  19

<210> SEQ ID NO 35
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 35
gagcttctct ttcgttcccg tttttctctt ggaaagaaag t                         41

<210> SEQ ID NO 36
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 36
tgtggagaag gagttcatag ctgttttttct cttggaaaga aagt                     44

<210> SEQ ID NO 37
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 37
agccccaggg agaaggcttt ttctcttgga aagaaagt                             38

<210> SEQ ID NO 38
<211> LENGTH: 42
<212> TYPE: DNA

-continued

```
<213> ORGANISM: Artificial
<220> FEATURE:
<223> OTHER INFORMATION: synthetic oligonucleotide probe

<400> SEQUENCE: 38 tgtctcctttt ctcagggctg atttttctct tggaaagaaa gt              42

<210> SEQ ID NO 39
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 39
cctcattgaa tccagattgg aattttctc ttggaaagaa agt               43

<210> SEQ ID NO 40
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 40
gaagagccct caggctggat ttttctcttg gaaagaaagt                  40
```

DETECTION OF NUCLEIC ACIDS THROUGH AMPLIFICATION OF SURROGATE NUCLEIC ACIDS

CROSS-REFERENCE TO RELATED APPLICATIONS

This application is a divisional of U.S. patent application Ser. No. 11/595,789, filed Nov. 9, 2006, entitled "DETECTION OF NUCLEIC ACIDS THROUGH AMPLIFICATION OF SURROGATE NUCLEIC ACIDS" by Yuling Luo and Son Bui, which issued on Sep. 13, 2011 as U.S. Pat. No. 8,017,360, and which claims priority to and benefit of the following prior provisional patent application: U.S. Ser. No. 60/735,808, filed Nov. 10, 2005, entitled "DETECTION OF NUCLEIC ACIDS THROUGH AMPLIFICATION OF SURROGATE NUCLEIC ACIDS" by Yuling Luo. Each of these applications is incorporated herein by reference in its entirety for all purposes.

FIELD OF THE INVENTION

The present invention is in the field of nucleic acid detection. The invention includes methods for detecting target nucleic acids by specifically associating surrogate nucleic acids with the target nucleic acids and then amplifying and detecting the surrogate nucleic acids. The invention also includes compositions and kits related to the methods.

BACKGROUND OF THE INVENTION

A wide variety of applications in basic biomedical and clinical research and in molecular medicine require specific detection of one or more nucleic acids (e.g., studies of gene expression). Levels of RNA expression, for example, have traditionally been measured using Northern blot and nuclease protection assays. However, these approaches are time-consuming and have limited sensitivity, and the data generated are more qualitative than quantitative in nature. A multiplex screening assay for mRNA was recently reported that combines nuclease protection with luminescent array detection (Martel et al. (2002) "Multiplexed screening assay for mRNA combining nuclease protection with luminescent array detection" Assay Drug Dev Technol. 1:61-71). However, although this assay has the advantage of measuring mRNA transcripts directly from cell lysates, limited assay sensitivity and reproducibility were reported.

Another exemplary technique, the real-time or quantitative polymerase chain reaction (qPCR), has been gaining widespread use in quantification of nucleic acid since its development (Higuchi et al. (1993) "Kinetic PCR analysis: Real-time monitoring of DNA amplification reactions" Biotechnology 11:1026-1030). This is primarily due to qPCR's excellent detection sensitivity and broad dynamic range, simple homogeneous assay format, and quantitative capability. However, the quantitative capability of the qPCR assay for mRNA is significantly compromised by the pre-analytical steps of RNA isolation and conversion to cDNA, which result in significant drops in assay reproducibility and accuracy (see, e.g., Bustin (2000) "Absolute quantification of mRNA using real-time reverse transcription polymerase chain reaction assays" Journal of Molecular Endocrinology 25:169-193, Bustin (2002) "Quantification of mRNA using real-time reverse transcription PCR (RT-PCR): Trends and problems" J Mol Endocrinol 29:23-39, and Bustin and Nolan (2004) "Pitfalls of quantitative real-time reverse-transcription polymerase chain reaction" J Biomol Tech. 15:155-66). There are several reasons why the pre-analytical steps potentially result in qPCR assay variations. First, isolated RNA can be of variable quality and stability. Second, the efficiency of conversion of RNA to cDNA is dependent on many factors, including reverse transcription enzyme efficiency, the presence of inhibitors in the reverse transcription reaction, template abundance, the presence of background nucleic acids, and different reverse transcription priming methods. Third, extensive degradation and modification of RNA can occur in samples such as formalin-fixed paraffin embedded tissue, which substantially affect the efficiency of RNA isolation from those samples and the quality of conversion of the isolated RNA to cDNA. Because of the need for RNA isolation and cDNA conversion in the current qPCR format, additional issues arise such as genomic DNA contamination, 3' bias, presence of inhibitors in the PCR reaction, interference by other cDNAs within the nucleic acid mixture, amplification efficiency variation among different samples, mispriming, and primer-dimer formation, among others.

Furthermore, the current qPCR format is based on target amplification, and, as a result, target-specific primers and probes need to be designed and validated for every target analyzed. Because the primers and probes are designed using a single gene sequence of limited genetic complexity, yet the PCR is conducted in the presence of a complex cDNA mixture, usually several primer and probe pairs need to be designed and validated in order to select a primer and probe pair with close to 100% amplification efficiency and no primer-dimer formation. In a multiplex qPCR format, mutual interference of multiple sets of PCR primers and probes can exacerbate the primer and probe selection problem, substantially increasing the amount of work required for assay design and validation. Also, a qPCR reaction for quantification of a particular target nucleic acid usually requires upfront optimization in primer and probe concentration, in $Mg^{2+}$ and dNTP concentrations, and in hot-start PCR to achieve highest amplification efficiency and to prevent mispriming and primer-dimer formation. Finally, assay reproducibility is particularly problematic when working with very low copy numbers of target nucleic acids because of stochastic effects. Particle distribution statistics predict that a greater number of replicates is required to differentiate five from 10 copies of a target molecule than to differentiate 500 from 1000 copies.

Therefore, there is a significant need to develop a qPCR and/or other nucleic acid detection method that eliminates the steps of RNA isolation and reverse transcription. There is also a significant need to develop a nucleic acid detection and/or quantification method that does not involve amplification of the target nucleic acid. Among other aspects, the present invention provides methods that overcome the above noted limitations and that permit rapid, simple, and sensitive detection and/or quantitation of nucleic acids. A complete understanding of the invention will be obtained upon review of the following.

SUMMARY OF THE INVENTION

In one aspect, the present invention provides methods of detecting target nucleic acids through capture and detection of surrogate nucleic acids. Compositions and kits related to the methods are also provided.

A first general class of embodiments provides methods of detecting a first target nucleic acid. In the methods, a first surrogate nucleic acid and a sample comprising the first target nucleic acid are provided. The first surrogate nucleic acid is physically associated with the first target nucleic acid, to provide captured first surrogate nucleic acid. The captured first surrogate nucleic acid is amplified to provide amplified first surrogate nucleic acid, and the amplified first surrogate nucleic acid is detected. Since the amount of amplified first surrogate nucleic acid is proportional to the amount of first surrogate nucleic acid captured on the first target nucleic acid, and therefore to the amount of first target nucleic acid, presence or amount of the amplified first surrogate nucleic acid detected provides an indication of presence or amount of the first target nucleic acid in the sample.

In one class of embodiments, the first surrogate nucleic acid is associated with the first target nucleic acid at a molar ratio of about 1:1. In another class of embodiments, the first surrogate nucleic acid is associated with the first target nucleic acid at a molar ratio of at least about 2:1, at least about 3:1, at least about 5:1, at least about 10:1, at least about 20:1, or more first surrogate nucleic acid:first target nucleic acid.

In a preferred aspect, a nucleic acid including the first surrogate nucleic acid is physically associated with the first target nucleic acid by hybridization of one or more surrogate capture probes to both nucleic acids. Thus, in one class of embodiments, a first set of one or more surrogate capture probes is provided. Each of the surrogate capture probes is capable of hybridizing simultaneously to the first target nucleic acid and to a nucleic acid comprising the first surrogate nucleic acid. The first set of one or more surrogate capture probes is hybridized to the first target nucleic acid and to the nucleic acid comprising the first surrogate nucleic acid, whereby the first surrogate nucleic acid is physically associated with the first target nucleic acid. The first set of surrogate capture probes optionally comprises two or more surrogate capture probes (e.g., three or more, four or more, five or more, or ten or more). Typically, the surrogate capture probes hybridize to nonoverlapping polynucleotide sequences in the first target nucleic acid.

In one class of embodiments, one or more copies of the nucleic acid comprising the first surrogate nucleic acid (and therefore of the first surrogate nucleic acid itself) are associated with a copy of the first target nucleic acid, the first set of surrogate capture probes comprises a subset of surrogate capture probes for each of the one or more copies of the nucleic acid comprising the first surrogate nucleic acid, and each subset of surrogate capture probes comprises n surrogate capture probes, where n is at least two. For example, n can be two, three, or more. In one class of embodiments, hybridizing each subset of n surrogate capture probes to a copy of the nucleic acid comprising the first surrogate nucleic acid associates that copy with the first target nucleic acid, while hybridization of n−1 of the n surrogate capture probes to the copy of the nucleic acid comprising the first surrogate nucleic acid does not associate it with the first target nucleic acid. Similarly, in one class of embodiments, hybridizing the first set of one or more surrogate capture probes to the first target nucleic acid and to the nucleic acid comprising the first surrogate nucleic acid is performed at a hybridization temperature which is greater than a melting temperature $T_m$ of a complex between each individual surrogate capture probe and the nucleic acid comprising the first surrogate nucleic acid.

The methods optionally include associating the first target nucleic acid with a solid support, e.g., a multiwell plate or a plurality of particles. At any of various steps, materials not associated with the solid support are optionally separated from the solid support. In one class of embodiments, a first set of m target capture probes capable of hybridizing to the first target nucleic acid, where m is at least one, is provided. The first set of target capture probes is hybridized with the first target nucleic acid, and the first set of target capture probes is associated with the solid support, associating the first target nucleic acid with the solid support. As noted, the first set of target capture probes includes m target capture probes, where m is at least one. Preferably, m is at least two. The m target capture probes in the first set preferably hybridize to nonoverlapping polynucleotide sequences in the first target nucleic acid.

In one class of embodiments, a first support capture probe is bound to the solid support, and the first set of target capture probes is associated with the solid support by hybridizing the target capture probes of the first set with the first support capture probe. In embodiments in which two or more target capture probes bind to the target nucleic acid, binding of a single target capture probe (or less than the full set of target capture probes) is optionally insufficient to capture the target nucleic acid to the solid support. Thus, in one class of embodiments in which m is at least two, hybridizing the first set of m target capture probes to the support capture probe captures the first target nucleic acid on the solid support, while hybridization of m−1 of the target capture probes to the support capture probe does not capture the first target nucleic acid on the solid support. Similarly, in one class of embodiments in which m is at least two, hybridizing the first set of target capture probes with the first support capture probe is performed at a hybridization temperature which is greater than a melting temperature $T_m$ of a complex between each individual target capture probe and the support capture probe.

The captured first surrogate nucleic acid can be amplified by essentially any convenient technique. As just one example, amplifying the captured first surrogate nucleic acid to provide amplified first surrogate nucleic acid and detecting the amplified first surrogate nucleic acid can comprise performing a quantitative real-time PCR experiment. The methods are optionally used to determine a relative amount or an absolute amount of the first target nucleic acid present in the sample.

The methods can be used to detect target nucleic acids from essentially any type of sample. The sample optionally includes a cell lysate, a tissue homogenate, an intercellular fluid, a bodily fluid, and/or a conditioned culture medium, and is optionally derived from a tissue (e.g., a formalin-fixed paraffin embedded tissue), a biopsy, and/or a tumor. Similarly, the target nucleic acid can be essentially any desired nucleic acid. As just a few examples, the first target nucleic acid can be derived from one or more of an animal, a human, a plant, a cultured cell, a microorganism, a virus, a bacterium, or a pathogen. The first target nucleic acid can be essentially any type of nucleic acid, e.g., a DNA, an RNA, or an mRNA. Similarly, the first surrogate nucleic acid can be essentially any type of nucleic acid, e.g., a DNA.

The methods can be conveniently multiplexed for detection of two or more target nucleic acids. Thus, in one aspect, the sample including the first target nucleic acid also includes a second target nucleic acid, and the methods include providing a second surrogate nucleic acid. The second surrogate nucleic acid is physically associated with the second target nucleic acid, to provide captured second surrogate nucleic acid. The captured second surrogate nucleic acid is amplified to provide amplified second surrogate nucleic acid, and the amplified second surrogate nucleic acid is detected. Presence or amount of the amplified second surrogate nucleic acid detected provides an indication of presence or amount of the second target nucleic acid in the sample. In one class of embodiments, detecting the amplified first surrogate nucleic acid and the amplified second surrogate nucleic acid comprises physically separating the amplified first surrogate nucleic acid from the amplified second surrogate nucleic acid. The methods optionally include providing, capturing, and amplifying third, fourth, fifth, etc. surrogate nucleic acids as well, such that from two to essentially any desired number of targets can be detected simultaneously.

Compositions useful in practicing or produced by the methods herein form another feature of the invention. Thus, another general class of embodiments provides a composition that includes a first target nucleic acid, a nucleic acid comprising a first surrogate nucleic acid, a first set of one or more surrogate capture probes, each of which is capable of hybridizing simultaneously to the first target nucleic acid and to the nucleic acid comprising the first surrogate nucleic acid, and one or more primers for amplifying the first surrogate nucleic acid.

The composition optionally also includes other reagents for amplifying the first surrogate nucleic acid, for example, a nucleic acid polymerase, nucleoside or deoxynucleoside triphosphates, and the like. It also optionally includes amplified first surrogate nucleic acid and/or one or more reagents for detecting the amplified first surrogate nucleic acid. In one class of embodiments, the composition includes a solid support to which the target and surrogate nucleic acids can be captured, for example, a multiwell plate or a plurality of particles.

Essentially any desired number of copies of the surrogate nucleic acid can be associated with each copy of the target nucleic acid. Thus, in one class of embodiments, the nucleic acid comprising the first surrogate nucleic acid is hybridized to the first set of surrogate capture probes, which surrogate capture probes are hybridized to the first target nucleic acid, whereby the first surrogate nucleic acid is physically associated with the first target nucleic acid at a molar ratio of about 1:1. In another class of embodiments, the nucleic acid comprising the first surrogate nucleic acid is hybridized to the first set of surrogate capture probes, which surrogate capture probes are hybridized to the first target nucleic acid, whereby the first surrogate nucleic acid is physically associated with the first target nucleic acid at a molar ratio of at least about 2:1, at least about 3:1, at least about 5:1, or at least about 10:1 first surrogate nucleic acid:first target nucleic acid.

Essentially all of the features described for the methods above apply to these embodiments as well, as relevant, for example, with respect to number and configuration of surrogate capture probes, number and configuration of target capture probes, support capture probes, types of target and surrogate nucleic acids, and/or the like.

It is worth noting that the composition optionally also includes a second nucleic acid comprising a second surrogate nucleic acid, a second set of one or more surrogate capture probes, each of which surrogate capture probes is capable of hybridizing simultaneously to a second target nucleic acid and to the second nucleic acid comprising the second surrogate nucleic acid, the second target nucleic acid, one or more primers for amplifying the second surrogate nucleic acid, amplified second surrogate nucleic acid, and/or one or more reagents for detecting the amplified second surrogate nucleic acid. Third, fourth, fifth, etc. target and surrogate nucleic acids, sets of surrogate capture probes, and the like are optionally also present in the composition.

Yet another general class of embodiments provides a kit for detecting at least one target nucleic acid. The kit includes a nucleic acid comprising a first surrogate nucleic acid, a first set of one or more surrogate capture probes, each of which is capable of hybridizing simultaneously to a first target nucleic acid and to the nucleic acid comprising the first surrogate nucleic acid, a solid support comprising a first support capture probe bound to the solid support, and a first set of m target capture probes, where m is at least one, which target capture probes are capable of hybridizing simultaneously to the first target nucleic acid and to the first support capture probe, packaged in one or more containers.

The kit optionally also includes one or more primers for amplifying the first surrogate nucleic acid, other reagents for amplifying the first surrogate nucleic acid (e.g., a nucleic acid polymerase, nucleoside or deoxynucleoside triphosphates, and the like), one or more reagents for detecting an amplified first surrogate nucleic acid (e.g., a dye or a fluorescently labeled primer or probe), a wash buffer for removing materials not specifically captured on the solid support, a lysis buffer for lysing cells and/or homogenizing tissues, the target and/or the surrogate nucleic acid at a standard concentration, and/or instructions for using the kit to detect and optionally quantitate one or more nucleic acids.

Essentially all of the features described for the methods and compositions above apply to these embodiments as well, as relevant, for example, with respect to the number of copies of the surrogate nucleic acid associated with each copy of the target nucleic acid, number and configuration of surrogate capture probes, number and configuration of target capture probes, support capture probes, types of target and surrogate nucleic acids, type of solid support, and/or the like.

It is worth noting that the kit optionally also includes a second nucleic acid comprising a second surrogate nucleic acid, a second set of one or more surrogate capture probes, each of which surrogate capture probes is capable of hybridizing simultaneously to a second target nucleic acid and to the second nucleic acid comprising the second surrogate nucleic acid, and a second set of m target capture probes, where m is at least one, which target capture probes are capable of hybridizing simultaneously to the second target nucleic acid and to the first support capture probe. One or more primers for amplifying the second surrogate nucleic acid and/or one or more reagents for detecting the amplified second surrogate nucleic acid can also be included in the kit, as can third, fourth, fifth, etc. target and surrogate nucleic acids, sets of target and surrogate capture probes, and the like.

BRIEF DESCRIPTION OF THE DRAWINGS

FIG. 2 Panels A-F depict an exemplary embodiment in which a target nucleic acid is captured on a solid support and a surrogate nucleic acid is physically associated with the target nucleic acid and then amplified.

Figure 1A:
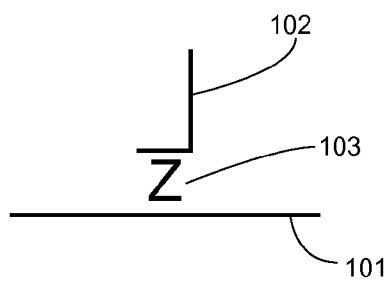
FIG. 1 Panels A-E schematically illustrate different schemes for physically associating one or more copies of a surrogate nucleic acid with a target nucleic acid.
Figure 1B:
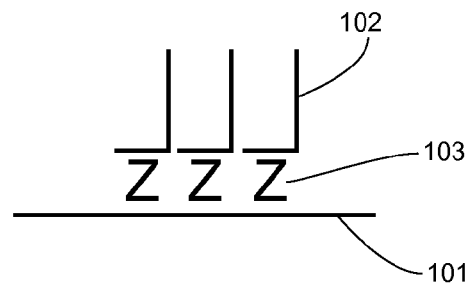
Figure 1C:
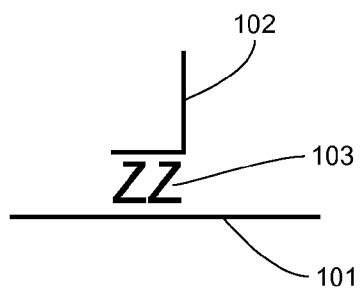
Figure 1D:
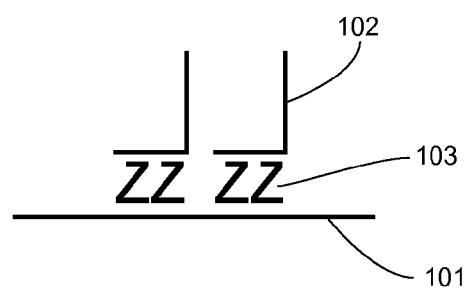
Figure 1E:
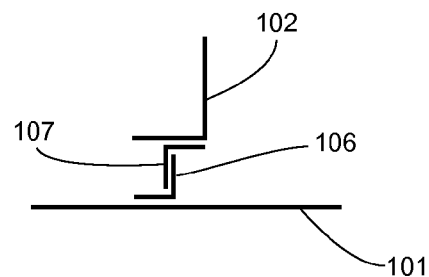
Figure 3A:
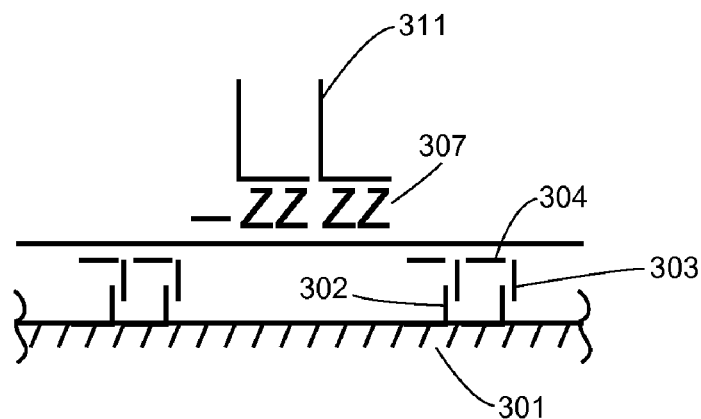
FIG. 3 Panel A schematically illustrates an exemplary setup for determining background. Panels B-D schematically illustrate exemplary potential sources of background.
Figure 3B:
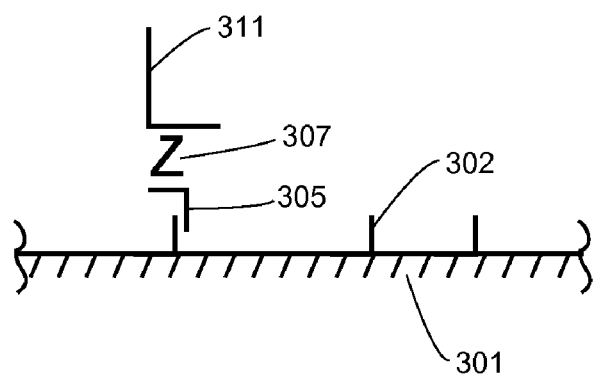
Figure 3C:
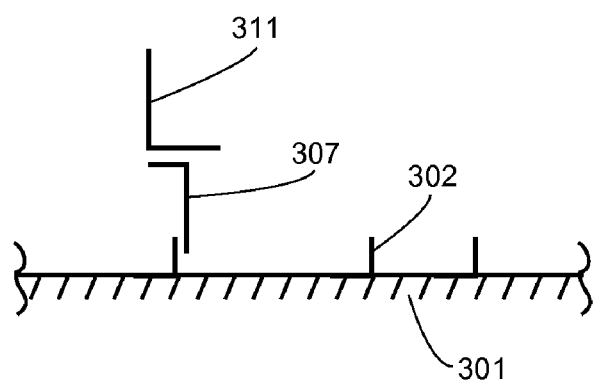
Figure 3D:
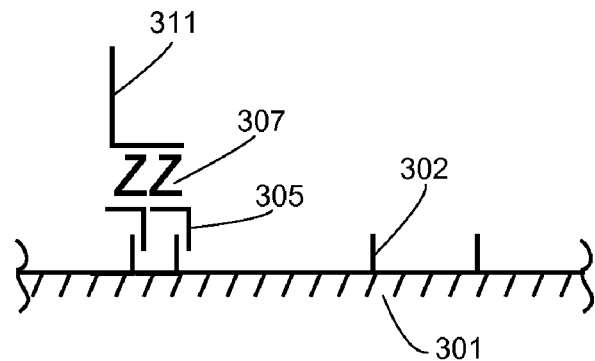

Figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "nucleic acid" (and the equivalent term "polynucleotide") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "target nucleic acid" is a nucleic acid to be detected, for example, via detection of a surrogate nucleic acid specifically associated with the target nucleic acid.

A "surrogate nucleic acid" is a nucleic acid that can be associated with a target nucleic acid and then amplified, to provide an indication of whether the target nucleic acid is present or in what amount the target nucleic acid is present. Preferably, neither the surrogate nucleic acid nor its complement hybridizes to the target nucleic acid under relevant assay conditions. The surrogate nucleic acid (and its complement) typically has less than 70% or less than 60%, and more typically, less than 50% sequence identity with the target nucleic acid. The surrogate nucleic acid is preferably single-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.), as well as in Ausubel, infra.

The "$T_m$" (melting temperature) of a nucleic acid duplex under specified conditions (e.g., relevant assay conditions) is the temperature at which half of the base pairs in a population of the duplex are disassociated and half are associated. The $T_m$ for a particular duplex can be calculated and/or measured, e.g., by obtaining a thermal denaturation curve for the duplex (where the $T_m$ is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "target capture probe" is a polynucleotide that is capable of hybridizing to a target nucleic acid. Typically, the target capture probe is capable of also simultaneously hybridizing to a support capture probe. The target capture probe typically has a first polynucleotide sequence U-1, which is complementary to the support capture probe, and a second polynucleotide sequence U-3, which is complementary to a polynucleotide sequence of the target nucleic acid. Sequences U-1 and U-3 are typically not complementary to each other. The target capture probe is preferably single-stranded.

A "support capture probe" is a polynucleotide that is capable of hybridizing to at least one target capture probe and that is tightly bound (e.g., covalently or noncovalently, directly or through a linker, e.g., streptavidin-biotin or the like) to a solid support, e.g., a multiwell plate, a slide, a particle, a microsphere, or the like. The support capture probe typically comprises at least one polynucleotide sequence U-2 that is complementary to polynucleotide sequence U-1 of at least one target capture probe. The support capture probe is preferably single-stranded.

A "surrogate capture probe" is a polynucleotide that is capable of hybridizing to a target nucleic acid and to a nucleic acid including a surrogate nucleic acid. The surrogate capture probe typically has a first polynucleotide sequence U-4, which is complementary to a polynucleotide sequence of the target nucleic acid, and a second polynucleotide sequence U-5, which is complementary to the nucleic acid including the surrogate nucleic acid. Sequences U-4 and U-5 are typically not complementary to each other. The surrogate capture probe is preferably single-stranded.

A nucleic acid is "amplified" when one or more additional nucleic acid molecules having a nucleotide sequence corresponding to that of the nucleic acid and/or its complement are produced. For example, a nucleic acid can be amplified in a template-dependent reaction in which a primer anneals to the nucleic acid and is extended by a nucleic acid polymerase to produce a copy of the nucleic acid's complement; optionally, another primer anneals to the complement and is extended to produce a copy of the nucleic acid. A single-stranded DNA molecule can be amplified, for example, by production of a complementary DNA strand or by production of a complementary RNA strand.

A first polynucleotide that is "capable of hybridizing" (or "configured to hybridize") to a second polynucleotide comprises a first polynucleotide sequence that is complementary to a second polynucleotide sequence in the second polynucleotide.

A "primer" is a nucleic acid that contains a sequence complementary to a region of a template nucleic acid strand and that primes the synthesis of a strand complementary to the template (or a portion thereof). Primers are typically, but need not be, relatively short, chemically synthesized oligonucleotides (typically, oligodeoxynucleotides). In order to be extendable by a standard polymerase, a primer typically has a free 3' hydroxyl group.

A "label" is a moiety that facilitates detection of a molecule. Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "microsphere" is a small spherical, or roughly spherical, particle. A microsphere typically has a diameter less than about 1000 micrometers (e.g., less than about 100 micrometers, optionally less than about 10 micrometers).

A "microorganism" is an organism of microscopic or submicroscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

A variety of additional terms are defined or otherwise characterized herein.

DETAILED DESCRIPTION

In one aspect, the invention provides methods for detecting and optionally quantitating a target nucleic acid. A surrogate nucleic acid is specifically associated with the target nucleic acid, and the surrogate nucleic acid is amplified and detected. The target nucleic acid is optionally associated with a solid support and need not be purified prior to association with the solid support and/or the surrogate nucleic acid. The methods of the invention can thus avoid problems associated with RNA isolation, reverse transcription, and the like. In addition, multiple copies of the surrogate nucleic acid are optionally associated with each copy of the target nucleic acid, improving sensitivity and precision when a low copy number target is to be detected. Compositions, kits, and systems related to the methods are also features of the invention.

Methods

One general class of embodiments provides methods of detecting a first target nucleic acid. In the methods, a first surrogate nucleic acid and a sample comprising the first target nucleic acid are provided. The first surrogate nucleic acid is physically associated with (e.g., indirectly bound or hybridized to) the first target nucleic acid, to provide captured first surrogate nucleic acid. The captured first surrogate nucleic acid is amplified to provide amplified first surrogate nucleic acid, and the amplified first surrogate nucleic acid is detected. Since the amount of amplified first surrogate nucleic acid is proportional to the amount of first surrogate nucleic acid captured on the first target nucleic acid, and therefore to the amount of first target nucleic acid, presence or amount of the amplified first surrogate nucleic acid detected provides an indication of presence or amount of the first target nucleic acid in the sample.

A single copy of the surrogate nucleic acid can be associated with each copy of the target nucleic acid. Thus, in one class of embodiments, the first surrogate nucleic acid is associated with the first target nucleic acid at a molar ratio of about 1:1. See, e.g., FIG. 1 Panels A, C, and E. Alternatively, however, multiple copies of the surrogate nucleic acid can be associated with each copy of the target nucleic acid, e.g., from two copies to essentially any desired preselected number of copies. Thus, in one class of embodiments, the first surrogate nucleic acid is associated with the first target nucleic acid at a molar ratio of at least about 2:1, about 3:1, about 5:1, about 10:1, about 20:1, or more first surrogate nucleic acid:first target nucleic acid. See, e.g., FIG. 1 Panels B and D.

In a preferred aspect, a nucleic acid including the first surrogate nucleic acid is physically associated with the first target nucleic acid by hybridization of one or more surrogate capture probes to both nucleic acids. Thus, in one class of embodiments, a first set of one or more surrogate capture probes is provided. Each of the surrogate capture probes is capable of hybridizing simultaneously to the first target nucleic acid and to a nucleic acid comprising the first surrogate nucleic acid. The first set of one or more surrogate capture probes is hybridized to the first target nucleic acid and to the nucleic acid comprising the first surrogate nucleic acid, whereby the first surrogate nucleic acid is physically associated with the first target nucleic acid. Hybridization of the surrogate capture probe(s) to the nucleic acids can occur simultaneously or sequentially, in either order. The first set of surrogate capture probes optionally comprises two or more surrogate capture probes (e.g., three or more, four or more, five or more, or ten or more). Typically, the surrogate capture probes hybridize to nonoverlapping polynucleotide sequences in the first target nucleic acid (see, e.g., FIG. 1 Panels B-D, which depict three exemplary binding arrangements of surrogate capture probes 103 to target nucleic acid 101 and a nucleic acid comprising surrogate nucleic acid 102). The nonoverlapping polynucleotide sequences are optionally, but need not be, contiguous.

The nucleic acid comprising the surrogate nucleic acid optionally consists of the surrogate nucleic acid. In such embodiments, the surrogate capture probe(s) hybridize to nucleotide sequences within the surrogate nucleic acid. Typically, however, the nucleic acid includes polynucleotide sequence U-6 in addition to the sequence of the surrogate nucleic acid, and the surrogate capture probe(s) are complementary to U-6 or subsequences within U-6. In one class of embodiments, the nucleic acid comprising the surrogate nucleic acid includes one copy of the surrogate nucleic acid, while in other embodiments, the nucleic acid comprising the surrogate nucleic acid includes two or more copies of the surrogate nucleic acid (e.g., two, three, five, 10, 20, or more copies). Thus, in embodiments in which multiple copies of the surrogate nucleic acid are associated with or captured to each copy of the target nucleic acid, more than one copy of the nucleic acid comprising the surrogate nucleic acid can be associated with the each copy of the target nucleic acid and/or each copy of the nucleic acid comprising the surrogate nucleic acid can include more than one copy of the surrogate nucleic acid.

Each copy of the nucleic acid comprising the surrogate nucleic acid is optionally associated with the target nucleic acid through hybridization of a single surrogate capture probe (see, e.g., FIG. 1 Panels A and B). Alternatively, each copy of the nucleic acid comprising the surrogate nucleic acid can be associated with the target nucleic acid through hybridization of two or more surrogate capture probes. Thus, in one class of embodiments, one or more copies of the nucleic acid comprising the first surrogate nucleic acid are associated with a copy of the first target nucleic acid, the first set of surrogate capture probes comprises a subset of surrogate capture probes for each of the one or more copies of the nucleic acid comprising the first surrogate nucleic acid, and each subset of surrogate capture probes comprises n surrogate capture probes, where n is at least two. For example, n can be two, three, or more. See, e.g., FIG. 1 Panels C and D. The surrogate capture probes within a given subset typically hybridize to nonoverlapping polynucleotide sequences in the nucleic acid comprising the first surrogate nucleic acid, as well as to nonoverlapping polynucleotide sequences in the first target nucleic acid. n is typically, but not necessarily, the same from subset to subset.

In embodiments in which two or more surrogate capture probes are used to capture each copy of the nucleic acid comprising the surrogate nucleic acid, binding of a single surrogate capture probe (or of less than the full subset of surrogate capture probes) is optionally too weak to stably capture the nucleic acid comprising the surrogate nucleic acid to the target nucleic acid. Thus, in one class of embodiments, hybridizing each subset of n surrogate capture probes to a copy of the nucleic acid comprising the first surrogate nucleic acid associates that copy with the first target nucleic acid, while hybridization of n−1 of the n surrogate capture probes to the copy of the nucleic acid comprising the first surrogate nucleic acid does not associate it with the first target nucleic acid. Similarly, in one class of embodiments, hybridizing the first set of one or more surrogate capture probes to the first target nucleic acid and to the nucleic acid comprising the first surrogate nucleic acid is performed at a hybridization temperature which is greater than a melting temperature $T_m$ of a complex between each individual surrogate capture probe and the nucleic acid comprising the first surrogate nucleic acid. For example, the hybridization temperature can be about 5° C. or more, about 7° C. or more, about 10° C. or more, about 15° C. or more, or about 20° C. or more greater than the $T_m$. In these embodiments, the $T_m$ of the complex between each individual surrogate capture probe and the first target nucleic acid is preferably significantly greater than the hybridization temperature such that each surrogate capture probe stably hybridizes to the target nucleic acid at the hybridization temperature. In alternative exemplary embodiments, binding of each individual surrogate capture probe to the first target nucleic acid is weak, while hybridization of each surrogate capture probe to the nucleic acid comprising the first surrogate nucleic acid is stable at the hybridization temperature.

It will be evident that a number of configurations for the surrogate capture probes are possible. For example, as illustrated in FIG. 1 Panels A-D, the 5' end of each surrogate capture probe can hybridize to the target nucleic acid while the 3' end is complementary to the nucleic acid comprising the surrogate nucleic acid (or vice versa). As another example, one surrogate capture probe can have its 5' end complementary to the target nucleic acid and its 3' end complementary to the nucleic acid comprising the surrogate nucleic acid, while another surrogate capture probe has its 3' end complementary to the target nucleic acid and its 5' end complementary to the nucleic acid comprising the surrogate nucleic acid, resulting in a cruciform arrangement. In yet another example, one oligonucleotide (106) hybridizes to the target nucleic acid and to another oligonucleotide (107) which in turn hybridizes to the nucleic acid comprising the surrogate nucleic acid (see FIG. 1 Panel E).

In one aspect, the target nucleic acid, and thus its associated surrogate nucleic acid, is captured on a solid support. Thus, in one class of embodiments, the methods include associating the first target nucleic acid with a solid support. Association of the target nucleic acid with the solid support and association of the surrogate nucleic acid with the target nucleic acid can occur simultaneously or sequentially, in either order.

Capture of the target nucleic acid to the solid support optionally involves hybridization of the target nucleic acid to target capture probes associated with the solid support. Thus, in one class of embodiments, a first set of m target capture probes capable of hybridizing to the first target nucleic acid, where m is at least one, is provided. The first set of target capture probes is hybridized with the first target nucleic acid, and the first set of target capture probes is associated with the solid support, associating the first target nucleic acid with the solid support. Hybridization of the target capture probes with the target nucleic acid and association of the target capture probes with the solid support can occur simultaneously or sequentially, in either order.

As noted, the first set of target capture probes includes m target capture probes, where m is at least one. Preferably, m is at least two or at least three, and m can be at least four or at least five or more. Typically, but not necessarily, m is at most ten. For example, m can be between three and ten, e.g., between five and ten or between five and seven, inclusive. Use of fewer target capture probes can be advantageous, for example, in embodiments in which the target nucleic acid is to be specifically captured from samples including other nucleic acids with sequences very similar to that of the target nucleic acid. In other embodiments (e.g., embodiments in which capture of as much of the target nucleic acid as possible is desired), however, m can be more than 10, e.g., between 20 and 50. The m target capture probes in the first set preferably hybridize to nonoverlapping polynucleotide sequences in the first target nucleic acid. The nonoverlapping polynucleotide sequences can, but need not be, consecutive within the target nucleic acid.

The target capture probes are optionally bound directly to the solid support (covalently or noncovalently), or they can be indirectly associated with the solid support. In one class of embodiments, a first support capture probe is bound to the solid support, and the first set of target capture probes is associated with the solid support by hybridizing the target capture probes of the first set with the first support capture probe.

In embodiments in which two or more target capture probes bind to the target nucleic acid, binding of a single target capture probe (or less than the full set of target capture probes) is optionally insufficient to capture the target nucleic acid to the solid support. Thus, in one class of embodiments in which m is at least two, hybridizing the first set of m target capture probes to the support capture probe captures the first target nucleic acid on the solid support, while hybridization of m−1 of the target capture probes to the support capture probe does not capture the first target nucleic acid on the solid support. Similarly, in one class of embodiments in which m is at least two, hybridizing the first set of target capture probes with the first support capture probe is performed at a hybridization temperature which is greater than a melting temperature $T_m$ of a complex between each individual target capture probe and the support capture probe. For example, the hybridization temperature can be about 5° C. or more, about 7° C. or more, about 10° C. or more, about 15° C. or more, or about 20° C. or more greater than the $T_m$. In these embodiments, the $T_m$ of the complex between each individual target capture probe and the first target nucleic acid is preferably significantly greater than the hybridization temperature such that each target capture probe stably hybridizes to the target nucleic acid at the hybridization temperature. In alternative exemplary embodiments, binding of each individual target capture probe to the first target nucleic acid is weak, while hybridization of each target capture probe to the first support capture probe is stable at the hybridization temperature.

In embodiments in which a support capture probe is employed, the target capture probe typically includes a polynucleotide sequence U-1 that is complementary to a polynucleotide sequence U-2 in the support capture probe. Sequences U-1 and U-2 can be of essentially any convenient length, depending, e.g., on the G-C base content of U-1 and U-2, on the hybridization temperature, and on whether hybridization between an individual target capture probe and support capture probe is desired to be strong or weak. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive). For example, U-1 and U-2 can be 14, 15, 16, or 17 nucleotides in length, or they can be between 9 and 13 nucleotides in length (e.g., for lower hybridization temperatures, e.g., hybridization at room temperature).

The support capture probe can include polynucleotide sequence in addition to U-2, or U-2 can comprise the entire polynucleotide sequence of the support capture probe. For example, each support capture probe optionally includes a linker sequence between the site of attachment of the support capture probe to the solid support and sequence U-2 (e.g., a linker sequence containing 8 Ts, as just one possible example).

It will be evident that the number of target capture probes required for stable capture of a target nucleic acid depends, in part, on the amount of overlap between the target capture probes and the support capture probe (i.e., the length of U-1 and U-2). For example, if m is 5-7 for a 14 nucleotide overlap, m could be 3-5 for a 15 nucleotide overlap or 2-3 for a 16 nucleotide overlap.

Stable capture of target nucleic acids, e.g., while minimizing capture of extraneous nucleic acids (e.g., those to which m−1 or fewer of the target capture probes bind) can be achieved, for example, by balancing m (the number of target capture probes), the amount of overlap between the target capture probes and the support capture probe (the length of U-1 and U-2), and/or the stringency of the conditions under which the target capture probes, the nucleic acids, and the support capture probes are hybridized.

Appropriate combinations of m, amount of complementarity between the target capture probes and the support capture probe, and stringency of hybridization can, for example, be determined experimentally by one of skill in the art. For example, a particular value of m and a particular set of hybridization conditions can be selected, while the number of nucleotides of complementarity between the target capture probes and the support capture probe is varied until hybridization of the m target capture probes to a nucleic acid captures the nucleic acid while hybridization of a single target capture probe (or optionally of m−1 target capture probes) does not efficiently capture the nucleic acid. Similarly, m, amount of complementarity, and stringency of hybridization can be selected such that the desired nucleic acid of interest is captured while other nucleic acids present in the sample are not efficiently captured. Stringency can be controlled, for example, by controlling the formamide concentration, chaotropic salt concentration, salt concentration, pH, organic solvent content, and/or hybridization temperature.

As noted, the $T_m$ of any nucleic acid duplex can be directly measured, using techniques well known in the art. For example, a thermal denaturation curve can be obtained for the duplex, the midpoint of which corresponds to the $T_m$. It will be evident that such denaturation curves can be obtained under conditions having essentially any relevant pH, salt concentration, solvent content, and/or the like.

The $T_m$ for a particular duplex (e.g., an approximate $T_m$) can also be calculated. For example, the $T_m$ for an oligonucleotide-target duplex can be estimated using the following algorithm, which incorporates nearest neighbor thermodynamic parameters: $T_m$ (Kelvin)=$\Delta H°/(\Delta S°+R \ln C_t)$, where the changes in standard enthalpy ($\Delta H°$) and entropy ($\Delta S°$) are calculated from nearest neighbor thermodynamic parameters (see, e.g., SantaLucia (1998) "A unified view of polymer, dumbbell, and oligonucleotide DNA nearest-neighbor thermodynamics" Proc. Natl. Acad. Sci. USA 95:1460-1465, Sugimoto et al. (1996) "Improved thermodynamic parameters and helix initiation factor to predict stability of DNA duplexes" Nucleic Acids Research 24: 4501-4505, Sugimoto et al. (1995) "Thermodynamic parameters to predict stability of RNA/DNA hybrid duplexes" Biochemistry 34:11211-11216, and et al. (1998) "Thermodynamic parameters for an expanded nearest-neighbor model for formation of RNA duplexes with Watson-Crick base pairs" Biochemistry 37: 14719-14735), R is the ideal gas constant (1.987 cal·K$^-$ $^1$mole$^{-1}$), and $C_t$ is the molar concentration of the oligonucleotide. The calculated $T_m$ is optionally corrected for salt concentration, e.g., Na$^+$ concentration, using the formula $1/T_m$ (Na$^+$)=$1/T_m$(1M)+(4.29f (G·C)−3.95)×10$^{-5}$ ln[Na$^+$]+9.40× 10$^{-6}$ ln$^2$[Na$^+$]. See, e.g., Owczarzy et al. (2004) "Effects of sodium ions on DNA duplex oligomers: Improved predictions of melting temperatures" Biochemistry 43:3537-3554 for further details. A web calculator for estimating $T_m$ using the above algorithms is available on the internet at scitools (dot) idtdna (dot) com/analyzer/oligocalc (dot) asp. Other algorithms for calculating $T_m$ are known in the art and are optionally applied to the present invention.

It will be evident that similar considerations apply to design of surrogate capture probes, above; for example, with respect to number of surrogate capture probes per subset (n), number of nucleotides of complementarity between the surrogate capture probe and the nucleic acid comprising the surrogate nucleic acid (length of U-5), and/or the stringency of the conditions under which the surrogate capture probes, the nucleic acid comprising the surrogate nucleic acid, and the target nucleic acid are hybridized.

The target capture probes and surrogate capture probes are preferably complementary to physically distinct, nonoverlapping sequences in the target nucleic acid, which can be, but are not necessarily, contiguous. The $T_m$s of the individual target capture probe-target nucleic acid and surrogate capture probe-target nucleic acid complexes are preferably greater than the hybridization temperature, e.g., by 5° C. or 10° C. or preferably by 15° C. or more, such that these complexes are stable at the hybridization temperature. Sequence U-3 for each target capture probe is typically (but not necessarily) about 17-35 nucleotides in length, with about 30-70% GC content. Similarly, sequence U-4 for each surrogate capture probe is typically (but not necessarily) about 17-35 nucleotides in length, e.g., about 20-30 nucleotides.

Potential target capture probe sequences (e.g., potential sequences U-3) are optionally examined for possible interactions with non-corresponding nucleic acids of interest, repetitive sequences (such as polyC or polyT, for example), any primers and/or detection probes used to amplify and/or detect the surrogate nucleic acid, and/or any relevant genomic sequences, for example; sequences expected to cross-hybridize with undesired nucleic acids are typically not selected for use in the target capture probes. Examination can be, e.g., visual (e.g., visual examination for complementarity), computational (e.g., computation and comparison of percent sequence identity and/or binding free energies; for example, sequence comparisons can be performed using BLAST software publicly available through the National Center for Biotechnology Information on the world wide web at www (dot) ncbi (dot) nlm (dot) nih (dot) gov), and/or experimental (e.g., cross-hybridization experiments). Potential surrogate, support capture probe, and surrogate capture probe sequences are preferably similarly examined, to ensure that undesirable cross-hybridization is not expected to occur.

A support capture probe, target capture probe, surrogate capture probe, and/or nucleic acid including a surrogate nucleic acid optionally comprises at least one non-natural nucleotide. For example, a support capture probe and the corresponding target capture probe optionally comprise, at complementary positions, at least one pair of non-natural nucleotides that base pair with each other but that do not Watson-Crick base pair with the bases typical to biological DNA or RNA (i.e., A, C, G, T, or U). Examples of nonnatural nucleotides include, but are not limited to, Locked NucleicAcid™ nucleotides (available from Exiqon A/S, on the world wide web at www (dot) exiqon (dot) com; see, e.g., SantaLucia Jr. (1998) Proc Natl Acad Sci 95:1460-1465) and isoG, isoC, and other nucleotides used in the AEGIS system (Artificially Expanded Genetic Information System, available from EraGen Biosciences, on the world wide web at www (dot) eragen (dot) com; see, e.g., U.S. Pat. Nos. 6,001,983, 6,037,120, and 6,140,496). Use of such non-natural base pairs (e.g., isoG-isoC base pairs) in the support capture probes and target capture probes (or the surrogate capture probes and nucleic acids including surrogate nucleic acids) can, for example, decrease cross hybridization, or it can permit use of shorter probes when the non-natural base pairs have higher binding affinities than do natural base pairs.

The solid support can be essentially any suitable support, including any of a variety of materials, configurations, and the like. For example, the solid support can comprise a multiwell plate or a plurality of particles (e.g., microspheres). Supports are discussed in greater detail in the section entitled "Solid supports" below.

At any of various steps, materials not associated with the solid support are optionally separated from the solid support. For example, after the target capture probes, target nucleic acid, and support-bound support capture probes are hybridized, the solid support is optionally washed to remove any unbound target capture probes and non-target nucleic acids. Similarly, the support can be washed after association of the surrogate nucleic acid with the target nucleic acid, to remove any unbound surrogate nucleic acid before amplification and detection of the surrogate.

The captured first surrogate nucleic acid can be amplified by essentially any convenient technique, depending, e.g., on the nature of the first surrogate nucleic acid (e.g., RNA or DNA), the technique to be used for detecting the amplified first surrogate nucleic acid, and/or the like. The first surrogate nucleic acid is preferably a DNA but can be an RNA or essentially any other form of nucleic acid. Similarly, the amplified first surrogate nucleic acid is preferably a DNA but can be an RNA or any other form of nucleic acid, and it can be single-stranded or double-stranded. One or more cycles of amplification can be performed, depending for example on the degree of amplification desired.

A wide variety of techniques for amplifying and detecting nucleic acids are known in the art and can be adapted to the practice of the present invention. Oligonucleotide primers, a nucleic acid polymerase, nucleoside or deoxynucleoside triphosphates, cofactors, aqueous buffered salt solutions, and the like are provided as appropriate for the selected technique, as is well-known in the art. As just a few examples, an RNA first surrogate nucleic acid can be amplified and the resulting double-stranded DNA amplified first surrogate nucleic acid detected using a reverse transcription-polymerase chain reaction (PCR) technique, e.g., a real-time reverse transcription-PCR technique, or a DNA first surrogate nucleic acid can be amplified by T7 polymerase, T3 polymerase, SP6 polymerase, strand displacement amplification, multiple-displacement amplification, or by rolling circle amplification (see, e.g., Hatch et al. (1999) "Rolling circle amplification of DNA immobilized on solid surfaces and its application to multiplex mutation detection" Genet Anal. 15:35-40; Baner et al. (1998) "Signal amplification of padlock probes by rolling circle replication" Nucleic Acids Res. 26:5073-8; Nallur et al. (2001) "Signal amplification by rolling circle amplification on DNA microarrays" Nucleic Acids Res. 29:E118; and Demidov and Broude, eds. (2004) DNA Amplification: Current Technologies and Applications, Horizon Bioscience.)

In one class of embodiments, amplifying the captured first surrogate nucleic acid involves one or more PCR cycles. In PCR, a pair of primers flanking the region to be amplified is typically provided. Template-dependent extension of the primers is catalyzed by a DNA polymerase, in the presence of deoxyribonucleoside triphosphates (typically dATP, dCTP, dGTP, and dTTP, although these can be replaced and/or supplemented with other dNTPs, e.g., a dNTP comprising a base analog that Watson-Crick base pairs like one of the conventional bases, e.g., uracil, inosine, or 7-deazaguanine), an aqueous buffer, and appropriate salts and metal cations (e.g., $Mg^{2+}$). The PCR process typically involves cycles of three steps: denaturation (e.g., of double-stranded template and/or extension product), annealing (e.g., of one or more primers to template), and extension (e.g., of one or more primers to form double-stranded extension products). The PCR process can instead, e.g., involve cycles of two steps: denaturation (e.g., of double-stranded template and/or extension product) and annealing/extension (e.g., of one or more primers to template and of one or more primers to form double-stranded extension products). The cycles are typically thermal cycles; for example, cycles of denaturation at temperatures greater than about 90° C., annealing at 50-75° C., and extension at 60-78° C. A thermostable enzyme is thus preferred. Such enzymes (including, e.g., *Thermus aquaticus* Taq DNA polymerase), appropriate buffers, etc. are widely commercially available, e.g., from Clontech (on the world wide web at www (dot) clontech (dot) com), Invitrogen (at www (dot) invitrogen (dot) com), Sigma-Aldrich (at www (dot) sigma-aldrich (dot) com), and New England Biolabs (at www (dot) neb (dot) com). PCR techniques have been extremely well described in both the patent and the scientific literature, and any of a variety of such techniques can be employed, including, e.g., asymmetric PCR.

In one class of embodiments, amplifying the captured first surrogate nucleic acid to provide amplified first surrogate nucleic acid and detecting the amplified first surrogate nucleic acid comprises performing a quantitative real-time PCR experiment. In real-time PCR, product formation is monitored in real time, for example, at a preselected point in each cycle. In real-time quantitative PCR with fluorescent detection of product, for example, a fluorescence threshold above background is typically assigned, and the time point at which each reaction's amplification plot reaches that threshold (defined as the threshold cycle number or Ct) is determined. The Ct value can be used to calculate the quantity of template initially present in each reaction. (Under a standard set of conditions, a lower or higher starting template concentration produces a higher or lower, respectively, Ct value.)

The methods are optionally used to determine a relative amount or an absolute amount of the first target nucleic acid present in the sample.

Real-time PCR techniques have been well described. See, e.g., the references noted above and Stephen A. Bustin, ed. (2004) A-Z of Quantitative PCR, International University Line, Edwards et al., eds. (2004) Real-Time PCR: An Essential Guide, Horizon Bioscience, and Klein (2002) "Quantification using real-time PCR technology: Applications and limitations" Trends in Molecular Medicine 8:257-260. In addition, automated thermal cyclers, including integrated systems for real time detection of product, are commercially available, e.g., the ABI Prism® 7700 sequence detection system from Applied Biosystems (on the world wide web at www (dot) appliedbiosystems (dot) com), the iCycler iQ® real-time PCR detection system from Bio-Rad (www (dot) biorad (dot) com), or the DNA Engine Opticon® continuous fluorescence detection system from MJ Research, Inc. (www (dot) mjr (dot) com).

The amplified first surrogate nucleic acid can be detected by any of a variety of techniques well known in the art. Detection optionally involves physical separation of the amplified surrogate nucleic acid from any other products of the amplification reaction, e.g., by electrophoresis, use of a fluorescent nucleic acid-binding dye, or binding of a labeled sequence-specific oligonucleotide probe, for example. In embodiments in which a real-time PCR technique is employed, the amplified surrogate nucleic acid can be detected using, for example, a fluorescent dye such as SYBR® green, ethidium bromide, or YO-PRO-1, or one or more fluorescently labeled oligonucleotide probes and/or primers, e.g., TaqMan® primers, scorpion primers, Hyb-Probes, Amplifluor® (sunrise) hairpin primers, molecular beacons, or Invader® oligonucleotides. See, e.g., Mackay et al. (2002) "Real-time PCR in virology" Nucleic Acids Res. 30:1292-1305, Poddar (2000) "Symmetric vs. asymmetric PCR and molecular beacon probe in the detection of a target gene of adenovirus" Molecular and Cellular Probes 14: 25-32, Nazarenko et al. (1997) "A closed tube format for amplification and detection of DNA based on energy transfer" Nucl. Acids Res. 25:2516-2521, Marras et al. (1999) "Multiplex detection of single-nucleotide variation using molecular beacons" Genet. Anal. Biomol. Eng. 14:151-156, Mhlanga et al. (2001) "Using molecular beacons to detect single-nucleotide polymorphisms with real-time PCR" Methods 25:463-471, Tyagi and Kramer (1996) "Molecular beacons: probes that fluoresce upon hybridization" Nature Biotechnology 14:303-308; Blok and Kramer (1997) "Amplifiable hybridization probes containing a molecular switch" Mol Cell Probes 11:187-194, Hsu et al. (2001) "Genotyping single-nucleotide polymorphisms by the Invader assay with dual-color fluorescence polarization detection" Clinical Chemistry 47:1373-1377, U.S. Pat. No. 5,691,146 (Nov. 25, 1997) to Mayrand entitled "Methods for combined PCR amplification and hybridization probing using doubly labeled fluorescent probes", U.S. Pat. No. 6,277,607 (Aug. 21, 2001) to Tyagi et al. entitled "High specificity primers, amplification methods and kits", U.S. Pat. No. 5,866,336 (Feb. 2, 1999) to Nazarenko et al. entitled "Nucleic acid amplification oligonucleotides with molecular energy transfer labels and methods based thereon", and references therein, among many other references.

An exemplary embodiment is schematically illustrated in FIG. 2. Panel A illustrates solid support 201 to which is bound support capture probe 202. Support capture probe 202 includes polynucleotide sequence U-2 (206). First set 203 of target capture probes is also illustrated. Each target capture probe includes sequences U-1 (204, complementary to the support capture probe's sequence U-2) and U-3 (205, complementary to a sequence in first target nucleic acid 210). Nucleic acid 211 includes surrogate nucleic acid 212 and sequence U-6 213. (As illustrated, nucleic acid 211 includes a single copy of the surrogate nucleic acid; in other embodiments, however, nucleic acid 211 optionally includes two or more copies of the surrogate nucleic acid sequence, for even greater amplification of the signal.) As depicted, first set 220 of surrogate capture probes includes four surrogate capture probes, one subset of two complementary to a first copy of nucleic acid 211 and another subset of two complementary to a second copy of nucleic acid 211 (which can have identical or distinct sequences U-6). Each of the exemplary surrogate capture probes includes polynucleotide sequence U-4 (221, complementary to a sequence in first target nucleic acid 210) at its 5' end, spacer sequence 222 (e.g., five Ts), and sequence U-5 (223, complementary to a sequence in region 213 of nucleic acid 211) at its 3' end.

The target capture probes are hybridized to the support capture probe and to the target nucleic acid, and the surrogate capture probes are hybridized to the target nucleic acid and the nucleic acid including the surrogate nucleic acid, simultaneously or sequentially (Panel B). Optional blocking probe 230 is hybridized to a region of target nucleic acid 210 not occupied by the target or support capture probes. Materials not captured on the solid support (e.g., non-target nucleic acid 240) are optionally separated from the support by washing.

Panels C-F schematically illustrate amplification of surrogate nucleic acid 212. The surrogate nucleic acid is optionally still associated with the solid support, or it is optionally removed from the solid support prior to amplification. Primer 250 is provided and annealed to surrogate nucleic acid 212 (Panel C). The primer is extended to produce complement 214 of surrogate nucleic acid 212 (Panel D). In embodiments in which only one cycle of amplification is performed and/or in which only a single primer is provided, complement 214 corresponds to the amplified first surrogate nucleic acid. Optionally, however, second primer 251 is also provided, and one or more additional cycles of denaturation, primer annealing, and extension are performed, e.g., by PCR, resulting in double-stranded amplification product 215 (Panels E and F). In such embodiments, product 215 typically corresponds to the amplified first surrogate nucleic acid to be detected. It will be evident that the pair of primers 250 and 251 define the 5' ends of amplification product 215. It will also be evident that the amount of amplified first surrogate nucleic acid is proportional to the amount of target nucleic acid initially present, the number of copies of the surrogate nucleic acid associated with each copy of the target nucleic acid, and the number of cycles of amplification performed.

As depicted in FIG. 2, the support capture probe includes a single sequence U-2 and thus hybridizes to a single target capture probe. Optionally, however, a support capture probe can include two or more sequences U-2 and hybridize to two or more target capture probes. Similarly, as depicted, each of the target capture probes in the first set includes an identical sequence U-1, and thus only a single support capture probe is needed; however, different target capture probes within a set optionally include different sequences U-1 and thus hybridize to different sequences U-2, within a single support capture probe or different support capture probes on the surface of the support.

One or more blocking probes, single-stranded oligonucleotides complementary to region(s) of the target nucleic acid not occupied by the target and surrogate capture probes, are optionally provided and hybridized to the target nucleic acid.

The regions of the target nucleic acid to which the target capture probes, surrogate capture probes, and blocking probes hybridize can, but need not be, contiguous.

The methods can be used to detect target nucleic acids from essentially any type of sample. For example, the sample can be derived from an animal, a human, a plant, a cultured cell, a virus, a bacterium, a pathogen, and/or a microorganism. The sample optionally includes a cell lysate, a tissue homogenate, an intercellular fluid, a bodily fluid (including, but not limited to, blood, serum, saliva, urine, sputum, or spinal fluid), and/or a conditioned culture medium, and is optionally derived from a tissue (e.g., a formalin-fixed paraffin embedded tissue), a biopsy, and/or a tumor. Similarly, the target nucleic acid can be essentially any desired nucleic acid. As just a few examples, the first target nucleic acid can be derived from one or more of an animal, a human, a plant, a cultured cell, a microorganism, a virus, a bacterium, or a pathogen. The first target nucleic acid can be essentially any type of nucleic acid, e.g., a DNA, an RNA, an mRNA, a bacterial or viral genomic RNA or DNA (double-stranded or single-stranded), a plasmid or other extra-genomic DNA, or another nucleic acid derived from a microorganism (pathogenic or otherwise). The nucleic acid can be purified, partially purified, or unpurified. It will be evident that a target nucleic acid that is initially double-stranded will typically be denatured before hybridization with target and/or surrogate capture probes.

The methods can be conveniently multiplexed for detection of two or more target nucleic acids. Thus, in one aspect, the sample including the first target nucleic acid also includes a second target nucleic acid, and the methods include providing a second surrogate nucleic acid. The second surrogate nucleic acid is physically associated with the second target nucleic acid, to provide captured second surrogate nucleic acid. The captured second surrogate nucleic acid is amplified to provide amplified second surrogate nucleic acid, and the amplified second surrogate nucleic acid is detected. Presence or amount of the amplified second surrogate nucleic acid detected provides an indication of presence or amount of the second target nucleic acid in the sample.

The methods optionally include providing, capturing, and amplifying third, fourth, fifth, etc. surrogate nucleic acids as well, such that from two to essentially any desired number of targets can be detected simultaneously. Essentially all of the features described for capture and amplification of the first surrogate nucleic acid above apply to the additional surrogate nucleic acids as well. For example, typically a second nucleic acid including the second surrogate nucleic acid and a second sequence U-6, distinct from that attached to the first surrogate nucleic acid, is provided, and a second set of surrogate capture probes complementary to the second target nucleic acid and to sequence(s) within U-6 is provided and used to associate the second surrogate and target nucleic acids. The second surrogate capture probes, second surrogate nucleic acid, and the like are preferably designed and/or tested to ensure minimal cross hybridization with the first surrogate nucleic acid, first target nucleic acid, and the like. It is worth noting than m and n can, but need not be the same between first and second sets or subsets of target and/or surrogate capture probes.

A number of the detection methods described above can be multiplexed. For example, primers and/or probes labeled with different fluorescent labels can be used to detect the amplified first and second surrogate nucleic acids. Typically, from two to four or five targets can be conveniently distinguished using fluorophores with distinct emission spectra. Alternatively, as another example, essentially any number of amplified surrogate nucleic acids can be physically separated and then detected, permitting multiplex detection of even large numbers of target nucleic acids simultaneously. Thus, in one class of embodiments, detecting the amplified first surrogate nucleic acid and the amplified second surrogate nucleic acid comprises physically separating the amplified first surrogate nucleic acid from the amplified second surrogate nucleic acid. Preferably, the amplified first and second surrogate nucleic acids contain different numbers of nucleotides, such that they can be conveniently separated based on their size. Separation can be performed, for example, in a commercially available capillary electrophoresis system, such as the GenomeLab™ GeXP multiplexed PCR system from Beckman Coulter (on the world wide web at www (dot) beckman (dot) com).

As another alternative, the captured surrogate nucleic acids can be separated from each other (e.g., by capturing the first and second target nucleic acids and thus the first and second surrogate nucleic acids on different subsets of identifiable particles or at different positions on a spatially addressable solid support, for example) and then amplified, prior to detection of the amplified surrogate nucleic acids.

The methods of the invention offer a number of advantages over current techniques for detecting and quantitating nucleic acids. For example, detection and quantitation of the target nucleic acid by capture and quantitation of a surrogate nucleic acid through quantitative real-time PCR (surrogate qPCR or sqPCR) has a number of advantages over traditional quantitative PCR in which the target itself is amplified. Because surrogate qPCR measures the target nucleic acid indirectly through quantification of a surrogate nucleic acid (a surrogate amplicon), it avoids issues related to target amplification by qPCR such as the necessity of primer/probe design and validation and assay optimization for every target. Because essentially any target nucleic acid can be quantified through a common surrogate amplicon, the surrogate nucleic acid, primers, and probes can be pre-designed and validated to possess close to 100% amplification efficiency and to ensure no primer-dimer formation or mispriming events. In addition, the methods can be adapted to a variety of different qPCR platforms such as SYBR® Green, TaqMan®, molecular beacon, scorpion, Lux probe, Qzyme, and the like.

Furthermore, use of surrogate nucleic acids avoids problems associated with design and validation of multiplex qPCR experiments. The surrogate qPCR methods described herein are well suited for multiplex analysis, because a common set of surrogate nucleic acids (surrogate amplicons), primers, and probes can be pre-designed and validated to ensure that they work together with close to 100% amplification efficiency and no mispriming or primer-dimer events. Once the standard set of amplicons is validated, essentially any combination of multiple nucleic acids can be detected and quantified without the need for substantial upfront assay design and validation work-only the relevant set of target capture probes, surrogate capture probes, and optional blocking probes need be synthesized for any new target nucleic acid. Only the probe sequences complementary to the desired target nucleic acid need be selected for each new target, since the probe sequences complementary to the support capture probes and nucleic acids including the surrogate nucleic acids would already have been designed and tested.

Surrogate qPCR is particularly well suited for quantifying mRNA because by quantifying a DNA surrogate nucleic acid, RNA isolation and conversion to cDNA by reverse transcription are avoided. The variations caused by the pre-analytical steps is thus eliminated, and assay accuracy and precision are therefore substantially improved. Additional issues associated with RNA isolation and cDNA conversion, such as genomic DNA contamination, 3' bias, interference from other cDNAs within the nucleic acid mixture, and amplification efficiency variation among different samples, are also avoided as a result of surrogate amplicon quantification.

Surrogate qPCR is well suited for absolute quantification of the copy number of a target nucleic acid in a sample by comparing PCR signal from the sample with PCR signal from a reference standard of surrogate amplicon. In surrogate qPCR, a standard curve is first constructed from surrogate amplicon of known concentrations. This curve is then used as a reference standard for extrapolating quantitative information for target nucleic acids of unknown concentrations. In standard qPCR assays, either RNA or cDNA standards are used for absolute quantification. Because these RNA or cDNA standards do not take into account the variations associated with RNA isolation and cDNA conversion in a real sample, they cannot give an accurate representation of the copy number of the intended target in the actual sample. In contrast, surrogate qPCR measures the same surrogate amplicon in reference standards as well as in a real sample; more accurate determination of copy number in the sample can thus be obtained.

Another advantage of surrogate qPCR is the "amplification" that is optionally achieved during target capture and hybridization with the surrogate amplicon. For example, in embodiments in which each copy of the target can bind to 10 or more copies of the surrogate amplicon, when 10 copies of the target RNA are to be detected, 100 or more copies of the surrogate amplicon are actually being quantified. (As just a few examples of configurations in which 10 copies of a surrogate amplicon are bound to each copy of a target nucleic acid, 10 copies of a nucleic acid that includes one copy of the amplicon can be associated with the target, one copy of a nucleic acid that includes 10 copies of the amplicon can be associated with the target, five copies of a nucleic acid that includes two copies of the amplicon can be associated with the target, or two copies of a nucleic acid that includes five copies of the amplicon can be associated with the target.) This additional amplification can minimize stochastic effects and improve assay precision when measuring low copy number target nucleic acids.

Relative quantification can also be determined by surrogate qPCR with high precision and accuracy because the target and the reference control use the same surrogate amplicon, so that the dynamic range as well as the amplification efficiency of the target and reference is the same.

Background from nonspecific binding events can readily be determined for the methods of the invention. For example, in surrogate qPCR, nonspecific binding of surrogate amplicon can optionally be determined and subtracted from the specific capture of surrogate amplicon to its target. Two general types of nonspecific binding events are predicted to potentially occur: nonspecific binding of the surrogate nucleic acid to the solid support, and undesirable probe-probe interactions. As shown in FIG. 3 Panel A, sample background is optionally determined by replacing target capture probes 305 with oligonucleotides 303 and 304, which correspond to sequences U-1 and U-3, respectively, of the target capture probes, so that target nucleic acid can not bind to the solid support specifically through target capture probe-support capture probe interactions. (In addition to the oligonucleotides and the target nucleic acid, Panel A depicts nucleic acid 311 including the surrogate nucleic acid, surrogate capture probes 307, support capture probes 302, and solid support 301.) In this situation, the only PCR signal left results from nonspecific binding, e.g., when the nucleic acid comprising the surrogate amplicon binds to the solid support nonspecifically. Because this assay background can be determined under exactly the same assay conditions as the assay signal, it facilitates accurate determination of PCR signal contributed by the specific capture of surrogate amplicon to its target. In this situation, even the amplification efficiency and PCR inhibition can be controlled to the same extent. Additional potential sources of background are shown in Panels B-D, probe background caused by probe-probe interactions that result in nonspecific capture of the surrogate nucleic acid to the solid support. Since probe background can be determined in the absence of sample input, it can be known and minimized prior to assaying the target nucleic acid in a sample. It is expected that probe background is generally low and can be negligible, particularly in embodiments in which two or more target capture probes and/or surrogate capture probes are required for stable capture of the target and/or surrogate nucleic acids. The background can determine the limit of detection of the surrogate qPCR assay, and is therefore preferably minimized.

Surrogate qPCR can be applied to most, if not all, traditional qPCR applications with higher assay accuracy and precision and greater ease of assay flow. For example, the methods of the invention can be applied to quantitative gene expression analysis, microarray verification and follow up, viral load determination, cancer diagnostics, pathogen detection, methylation detection, genotyping, GMO (genetically modified organism) copy number determination, gene amplification and deletion, quantitative microsatellite analysis, prenatal diagnosis, single cell expression analysis, and the like. Importantly, surrogate qPCR (and similar methods of the invention) provides an excellent platform for multiplex analysis in such applications.

Compositions

Compositions useful in practicing or produced by the methods herein form another feature of the invention. Thus, one general class of embodiments provides a composition that includes a first target nucleic acid, a nucleic acid comprising a first surrogate nucleic acid, a first set of one or more surrogate capture probes, each of which is capable of hybridizing simultaneously to the first target nucleic acid and to the nucleic acid comprising the first surrogate nucleic acid, and one or more primers for amplifying the first surrogate nucleic acid.

The composition optionally also includes other reagents for amplifying the first surrogate nucleic acid, for example, a nucleic acid polymerase, nucleoside or deoxynucleoside triphosphates, and the like. It also optionally includes amplified first surrogate nucleic acid and/or one or more reagents for detecting the amplified first surrogate nucleic acid. Exemplary detection reagents include, but are not limited to, dyes, fluorescent primers, and fluorescent probes such as those noted above.

Essentially any desired number of copies of the surrogate nucleic acid can be associated with each copy of the target nucleic acid. Thus, in one class of embodiments, the nucleic acid comprising the first surrogate nucleic acid is hybridized to the first set of surrogate capture probes, which surrogate capture probes are hybridized to the first target nucleic acid, whereby the first surrogate nucleic acid is physically associated with the first target nucleic acid at a molar ratio of about 1:1. In another class of embodiments, the nucleic acid comprising the first surrogate nucleic acid is hybridized to the first set of surrogate capture probes, which surrogate capture probes are hybridized to the first target nucleic acid, whereby the first surrogate nucleic acid is physically associated with the first target nucleic acid at a molar ratio of at least about 2:1, at least about 3:1, at least about 5:1, or at least about 10:1 first surrogate nucleic acid:first target nucleic acid. As in the methods described above, the nucleic acid comprising the surrogate nucleic acid can include one copy of the surrogate nucleic acid, or it can include two or more copies of the surrogate nucleic acid. Thus, in embodiments in which multiple copies of the surrogate nucleic acid are associated with or captured to each copy of the target nucleic acid, more than one copy of the nucleic acid comprising the surrogate nucleic acid can be associated with the each copy of the target nucleic acid and/or each copy of the nucleic acid comprising the surrogate nucleic acid can include more than one copy of the surrogate nucleic acid.

In one class of embodiments, the composition includes a solid support to which the target and surrogate nucleic acids can be (or are) captured, for example, a multiwell plate or a plurality of particles. Exemplary supports are provided in the section entitled "Solid supports" below.

Essentially all of the features described for the methods above apply to these embodiments as well, as relevant, for example, with respect to number and configuration of surrogate capture probes, number and configuration of target capture probes, support capture probes, types of target and surrogate nucleic acids, optional blocking probes, and/or the like.

It is worth noting that the composition optionally also includes a second nucleic acid comprising a second surrogate nucleic acid, a second set of one or more surrogate capture probes, each of which surrogate capture probes is capable of hybridizing simultaneously to a second target nucleic acid and to the second nucleic acid comprising the second surrogate nucleic acid, the second target nucleic acid, one or more primers for amplifying the second surrogate nucleic acid, amplified second surrogate nucleic acid, and/or one or more reagents for detecting the amplified second surrogate nucleic acid. Third, fourth, fifth, etc. target and surrogate nucleic acids, sets of surrogate capture probes, and the like are optionally also present in the composition.

Kits

Yet another general class of embodiments provides a kit for detecting at least one target nucleic acid. The kit includes a nucleic acid comprising a first surrogate nucleic acid, a first set of one or more surrogate capture probes, each of which is capable of hybridizing simultaneously to a first target nucleic acid and to the nucleic acid comprising the first surrogate nucleic acid, a solid support comprising a first support capture probe bound to the solid support, and a first set of m target capture probes, where m is at least one, which target capture probes are capable of hybridizing simultaneously to the first target nucleic acid and to the first support capture probe, packaged in one or more containers.

The kit optionally also includes one or more primers for amplifying the first surrogate nucleic acid, other reagents for amplifying the first surrogate nucleic acid (e.g., a nucleic acid polymerase, nucleoside or deoxynucleoside triphosphates, and the like), one or more reagents for detecting an amplified first surrogate nucleic acid (e.g., a dye or a fluorescently labeled primer or probe), a wash buffer for removing materials not specifically captured on the solid support, a lysis buffer for lysing cells and/or homogenizing tissues, the target and/or the surrogate nucleic acid at a standard concentration, and/or instructions for using the kit to detect and optionally quantitate one or more nucleic acids.

Essentially all of the features described for the methods and compositions above apply to these embodiments as well, as relevant, for example, with respect to the number of copies of the surrogate nucleic acid associated with each copy of the target nucleic acid, number and configuration of surrogate capture probes, number and configuration of target capture probes, support capture probes, types of target and surrogate nucleic acids, type of solid support, optional blocking probes, and/or the like.

It is worth noting that the kit optionally also includes a second nucleic acid comprising a second surrogate nucleic acid, a second set of one or more surrogate capture probes, each of which surrogate capture probes is capable of hybridizing simultaneously to a second target nucleic acid and to the second nucleic acid comprising the second surrogate nucleic acid, and a second set of m target capture probes, where m is at least one, which target capture probes are capable of hybridizing simultaneously to the second target nucleic acid and to the first support capture probe (or, alternatively, to a second support capture probe bound to the solid support). One or more primers for amplifying the second surrogate nucleic acid and/or one or more reagents for detecting the amplified second surrogate nucleic acid can also be included in the kit, as can third, fourth, fifth, etc. target and surrogate nucleic acids, sets of target and surrogate capture probes, and the like.

Systems

In one aspect, the invention includes systems, e.g., systems used to practice the methods herein and/or comprising the compositions described herein. The system can include, e.g., a fluid and/or particle handling element, a fluid and/or particle containing element, a laser for exciting a fluorescent label or labels, a detector for detecting fluorescent emissions from a fluorescent label or labels, a thermal cycler, a capillary electrophoresis instrument, and/or a robotic element that moves other components of the system from place to place as needed (e.g., a multiwell plate handling element). For example, in one class of embodiments, a composition of the invention is contained in a thermal cycler, a microplate reader, or like instrument. In one class of embodiments, the system automates capture, amplification, and/or detection of one or more target nucleic acids.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, thermal cycler, robotic element, and/or laser). The computer can also receive data from other components of the system, e.g., from a detector, and can interpret the data, provide it to a user in a human readable format, or use that data to initiate further operations, in accordance with any programming by the user.

Solid Supports

Certain embodiments described herein employ a solid support. The solid support can be essentially any suitable support, including any of a variety of materials, configurations, and the like. For example, in one class of embodiments, the solid support is a substantially planar solid support, e.g., an upper surface of the bottom of a well of a multiwell plate, a slide, a membrane, or the like. Similarly, suitable solid supports include any surface of a well of a multiwell plate, whether planar or not. As another example, the solid support can comprise a plurality of particles, e.g., microspheres, beads, cylindrical particles, irregularly shaped particles, or the like. Optionally, the particles (or other solid support) are functionalized, for example, for ease of attachment of support or target capture probes. The particles optionally have additional or other desirable characteristics. For example, the particles can be magnetic or paramagnetic, providing a convenient means for separating the particles from solution, e.g., to simplify separation of the particles from any materials not bound to the particles. Similarly, for example, individual particles or sets of particles are optionally identifiable, e.g., by an embedded fluorescent or other code. The solid support is optionally spatially addressable.

A variety of suitable solid supports are commercially readily available. For example, microspheres with a variety of surface chemistries are commercially available, e.g., from Dynal (on the world wide web at www (dot) dynalbiotech (dot) com; microspheres available include carboxylated magnetic Dynabeads® with surface streptavidin), Polysciences, Inc. (on the world wide web at www (dot) polysciences (dot) com) or Luminex Corporation (on the world wide web at www (dot) luminexcorp (dot) com; microspheres available include fluorescently coded, identifiable sets of microspheres). For example, microspheres with carboxyl or amino groups are available and permit covalent coupling of molecules (e.g., polynucleotide probes with free reactive groups) to the microspheres. As another example, microspheres with surface streptavidin are available and can bind biotinylated capture probes; similarly, microspheres coated with biotin are available for binding capture probes conjugated to avidin or streptavidin. As another example, surface-modified and pre-coated slides with a variety of surface chemistries are commercially available, e.g., from TeleChem International (on the world wide web at www (dot) arrayit (dot) com), Corning, Inc. (Corning, N.Y.), or Greiner Bio-One, Inc. (on the world wide web at www (dot) greinerbiooneinc (dot) com). For example, silanated and silyated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated capture probes. As yet another example, surface-modified and pre-coated multiwell plates are commercially available, e.g., from Sigma-Aldrich, Inc. (on the world wide web at www (dot) sigmaaldrich (dot) com). For example, streptavidin and poly-D-lysine coated multiwell plates are available.

Protocols for using such commercially available microspheres, plates, and slides (e.g., methods of covalently coupling polynucleotides to carboxylated microspheres for use as capture probes, methods of blocking reactive sites on the support surface that are not occupied by the polynucleotides, methods of binding biotinylated polynucleotides to avidin-functionalized supports, and the like) are typically supplied with the supports and are readily utilized and/or adapted by one of skill. In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Kellar and Iannone (2002) "Multiplexed microsphere-based flow cytometric assays" Experimental Hematology 30:1227-1237; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.), and various vectors, cell lines and the like useful in manipulating and making nucleic acids are described in the above references. In addition, essentially any polynucleotide (including, e.g., labeled or biotinylated polynucleotides) can be custom or standard ordered from any of a variety of commercial sources, such as The Midland Certified Reagent Company (on the world wide web at www (dot) mcrc (dot) com), The Great American Gene Company (on the world wide web at www (dot) genco (dot) com), ExpressGen Inc. (on the world wide web at www (dot) expressgen (dot) com), Qiagen (on the internet at oligos (dot) qiagen (dot) com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology (on the world wide web at www (dot) piercenet (dot) com). Similarly, any nucleic acid can be fluorescently labeled, for example, by using commercially available kits such as those from Molecular Probes/Invitrogen (at probes (dot) invitrogen (dot) com/) or Pierce Biotechnology (on the world wide web at www (dot) piercenet (dot) com) or by incorporating a fluorescently labeled phosphoramidite during chemical synthesis of a polynucleotide.

Specialized primers and probes can also be custom or standard ordered from any of a variety of commercial sources. For example, custom TaqMan® primers can be ordered from Applied Biosystems (on the world wide web at www (dot) appliedbiosystems (dot) com), molecular beacons from Integrated DNA Technologies or The Midland Certified Reagent Company (on the world wide web at www (dot) idtdna (dot) com and www (dot) oligos (dot) com, respectively), Invader® oligonucleotides from Third Wave Technologies, Inc. (on the world wide web at www (dot) twt (dot) com), and scorpion primers from DxS (on the world wide web at www (dot) dxsgenotyping (dot) com), as just a few examples.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Detection of a Nucleic Acid Target Using Surrogate QPCR

The following sets forth a series of experiments that demonstrate detection of an IL-6 RNA target by capturing a surrogate nucleic acid to the IL-6 target and then amplifying the captured surrogate nucleic acid and detecting the amplified surrogate nucleic acid, using quantitative real-time PCR.

Materials

The sequence of the nucleic acid comprising the surrogate nucleic acid was 5'CGGGTATGGCTTTCATGTGGTTCTGGACAATGACGGTTACGGAGGTGGGCGTGGTCGTCTGCTGGGTTGGTCACGTGGGCGATCGACTTTTTAAAACGGTAACTTCATGCTTTGACTCAG (SEQ ID NO:1); 5T separate the surrogate nucleic acid (the surrogate amplicon, underlined) and the sequence U-6 that binds to the surrogate capture probe. Primers used for qPCR amplification of the surrogate amplicon were as follows: forward primer 5' CGGGTATGGCTTTCATGTGGT (SEQ ID NO:2) and reverse primer 5' gtcgatcgcccacgtgac (SEQ ID NO:3). In vitro transcribed (IVT) IL-6 RNA was used as the target nucleic acid, in the indicated amounts. The sequence of the support capture probe was 5' TTTTT-Tactttctttccaagag (SEQ ID NO:4). Sequences of the target capture probes, surrogate capture probes, and blocking probes are listed in Table 1.

TABLE 1

Sequences of IL-6 probe set: target capture probes (TCP), surrogate capture probes (SCP), and blocking probes (BP).

| | | |
|---|---|---|
| SEQ ID NO: 5 | SCP | aagaggtgagtggctgtctgtgTTTTTctgagtcaaagcatgaagttaccgtttt |
| SEQ ID NO: 6 | SCP | gaatttgtttgtcaattcgttctgTTTTTctgagtcaaagcatgaagttaccgtttt |
| SEQ ID NO: 7 | SCP | atctgttctggaggtactctaggtataTTTTTctgagtcaaagcatgaagttaccgtttt |
| SEQ ID NO: 8 | SCP | ggcttgttcctcactactctcaaTTTTTctgagtcaaagcatgaagttaccgtttt |
| SEQ ID NO: 9 | SCP | ctgcaggaactggatcaggacTTTTTctgagtcaaagcatgaagttaccgtttt |
| SEQ ID NO: 10 | SCP | gcatctagattctttgccttttTTTTTctgagtcaaagcatgaagttaccgtttt |
| SEQ ID NO: 11 | SCP | tgtgcctgcagcttcgtcaTTTTTctgagtcaaagcatgaagttaccgtttt |
| SEQ ID NO: 12 | SCP | tgtcctgcagccactggttcTTTTTctgagtcaaagcatgaagttaccgtttt |
| SEQ ID NO: 13 | SCP | ggtttctgaccagaagaaggaatgTTTTTctgagtcaaagcatgaagttaccgtttt |
| SEQ ID NO: 14 | SCP | aagttctgtgcccagtggacaTTTTTctgagtcaaagcatgaagttaccgtttt |
| SEQ ID NO: 15 | BP | TGGGGCAGGGAAGGCA |
| SEQ ID NO: 16 | BP | GGAATCTTCTCCTGGGGGTAC |
| SEQ ID NO: 17 | BP | TGGGGCGGCTACATCTTT |
| SEQ ID NO: 18 | BP | GCTTTCACACATGTTACTCTTGTTACA |
| SEQ ID NO: 19 | BP | TTTGGAAGGTTCAGGTTGTTTT |
| SEQ ID NO: 20 | BP | CCTCAAACTCCAAAAGACCAGTG |
| SEQ ID NO: 21 | BP | TTGGGTCAGGGGTGGTTATT |
| SEQ ID NO: 22 | BP | CTGCAGGAACTCCTTAAAGCTG |
| SEQ ID NO: 23 | BP | CCCATTAACAACAACAATCTGAGG |
| SEQ ID NO: 24 | BP | ggctcctggaggcgagata |
| SEQ ID NO: 25 | BP | aactggaccgaaggcgct |
| SEQ ID NO: 26 | BP | gcaggcaacaccaggagc |
| SEQ ID NO: 27 | BP | gatgccgtcgaggatgtacc |

TABLE 1-continued

Sequences of IL-6 probe set: target capture probes (TCP), surrogate capture probes (SCP), and blocking probes (BP).

| SEQ ID NO: 28 | BP  | ctgccagtgcctctttgct |
| SEQ ID NO: 29 | BP  | gcatccatcttttcagccatc |
| SEQ ID NO: 30 | BP  | atgattttcaccaggcaagtct |
| SEQ ID NO: 31 | BP  | ttttgtactcatctgcacagctct |
| SEQ ID NO: 32 | BP  | gcaggctggcatttgtgg |
| SEQ ID NO: 33 | BP  | cgcagaatgagatgagttgtca |
| SEQ ID NO: 34 | BP  | tgcccatgctacatttgcc |
| SEQ ID NO: 35 | TCP | gagcttctctttcgttcccgTTTTTctcttggaaagaaagt |
| SEQ ID NO: 36 | TCP | tgtggagaaggagttcatagctgTTTTTctcttggaaagaaagt |
| SEQ ID NO: 37 | TCP | agccccagggagaaggcTTTTTctcttggaaagaaagt |
| SEQ ID NO: 38 | TCP | tgtctcctttctcagggctgaTTTTTctcttggaaagaaagt |
| SEQ ID NO: 39 | TCP | cctcattgaatccagattggaaTTTTTctcttggaaagaaagt |
| SEQ ID NO: 40 | TCP | gaagagccctcaggctggaTTTTTctcttggaaagaaagt |

To conjugate magnetic beads with support capture probe, Dynal Dynabeads® M270 carboxylic acid beads were conjugated with 5' amine labeled support capture probe according to Flagella et al. (2006) "A multiplex branched DNA assay for parallel quantitative gene expression profiling" Anal Biochem. 352:50-60. Briefly, $2.5 \times 10^8$ beads were resuspended in 200 µl 0.1 M MES, pH 4.5, and incubated in the presence of ~8 µM support capture probe and 2 mg/ml 1-ethyl-3-(3-dimethylaminopropyl) carbodiimide hydrochloride (Pierce, Rockford, Ill.).

Surrogate qPCR

Figure 4A:
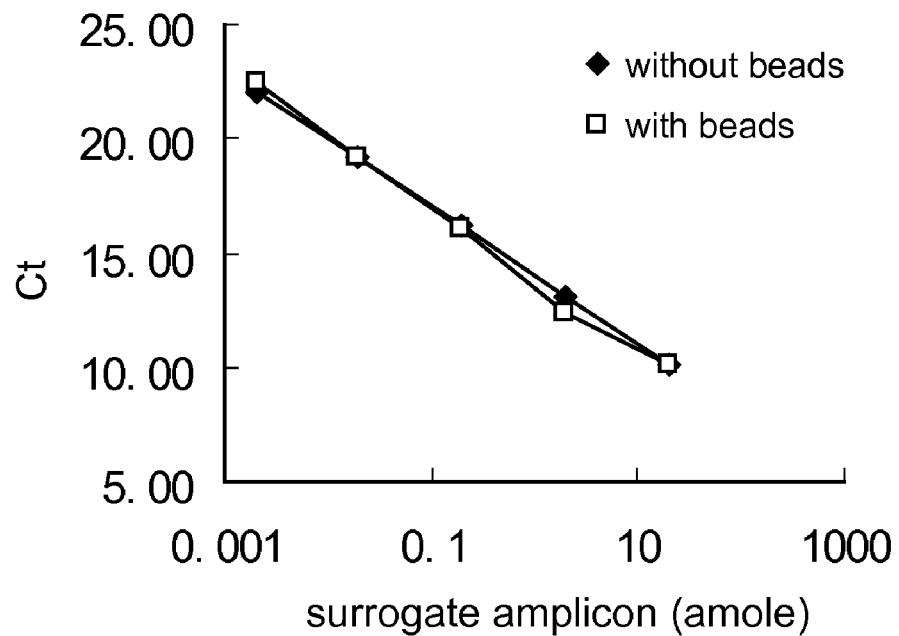
FIG. 4 Panel A presents a graph illustrating that inclusion of magnetic beads in a qPCR reaction has minimal effect. Panel B presents a graph illustrating detection of an IL-6 RNA target by capture and amplification of a surrogate nucleic acid.
Figure 4B:
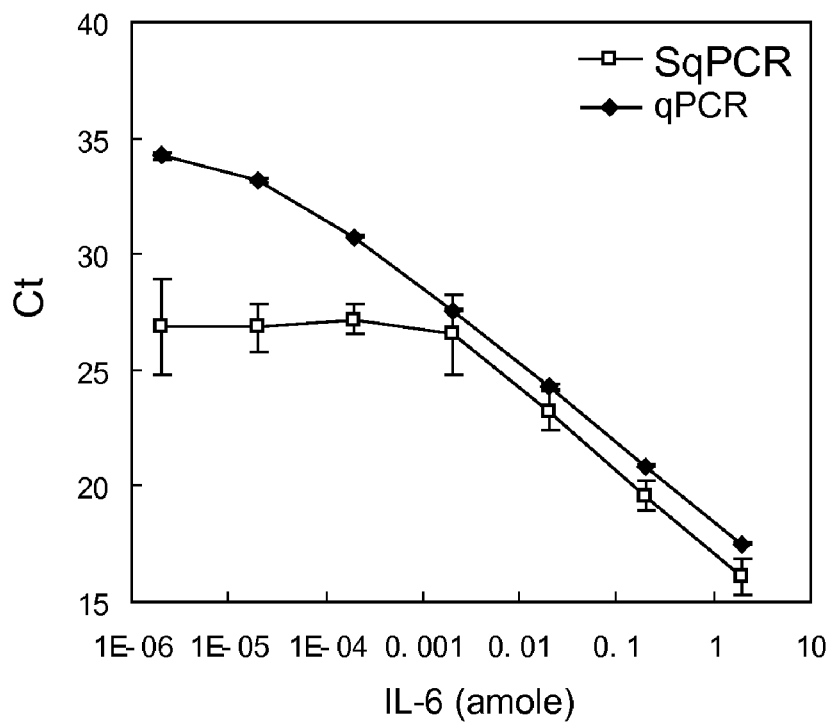

An initial experiment was performed to determine whether surrogate nucleic acids captured to target nucleic acids bound to magnetic bead solid supports could be amplified in the presence of the beads or whether the surrogate nucleic acid would need to be isolated from the beads prior to amplification. Surrogate nucleic acid was amplified by SYBR® green qPCR in the presence (squares) or absence (diamonds) of approximately one million magnetic beads, and, as shown in FIG. 4 Panel A, the presence of magnetic beads in qPCR reactions had minimal effect. In subsequent experiments, amplification of surrogate nucleic acid captured to beads was therefore performed in the presence of the beads.

Samples containing IL-6 IVT RNA were mixed with the pooled probe set (the target capture probes, surrogate capture probes, and blocking probes) and capture beads (support capture probe-conjugated magnetic beads, 300,000 beads per assay) and hybridized for 16 hours at 53° C. in 100 µL volume. The components in a 100 µl IVT RNA assay were 33% v/v lysis mixture, 40% v/v capture buffer, 1 µg tRNA, and the panel-specific probe set (target capture probe, 0.165 fmol/µl; surrogate capture probe, 0.66 fmol/µl; blocking probe, 0.33 fmol/µl). Lysis mixture and capture buffer commercially available from Panomics, Inc. (www (dot) panomics (dot) com), e.g., as catalog numbers QG0502 and QG0518, respectively, were used in these experiments, but it will be evident that any of a variety of similar suitable solutions can be employed (for example, the capture diluent described in Collins et al. (1997) Nucleic Acid Research 25:2979-2984 (127 mM LiCl, 5% lithium lauroyl sulfate, 9 mM EDTA, 50 mM HEPES (pH 7.5), 0.05% hespan (DuPont Pharmaceuticals), 0.05% ProClin 300 (Supelco), 0.2% casein (Research Organics, Hammarsten quality) is optionally employed as the lysis mixture and/or 50 mM HEPES acid, 50 mM HEPES sodium salt, 1% lithium lauryl sulfate, 8 mM EDTA, 0.3% nucleic acid blocking agent (Roche), and 0.5% Micro-O-protect is optionally employed as the capture buffer).

After the overnight hybridization step, unbound materials were washed from the beads (complexed with the probe set and IL-6 target RNA) using a magnetic separator and addition of wash buffer (0.1×SSC, 0.03% lithium lauryl sulfate). Five washes were performed. The beads were then incubated with 100 fmol of the nucleic acid molecule including the surrogate nucleic acid in amplifier/label probe diluent (Panomics catalog number QG0505; 3M tetramethyl ammonium chloride, 0.1% Sarkosyl, 50 mM Tris-HCl, 4 mM EDTA, 4% dextran sulfate, 1% BSA and 0.5% v/v Micr-O-protect (Roche Molecular Systems, Pleasanton, Calif.) is optionally employed instead) for 1 hour at 46° C. After the hybridization with surrogate nucleic acid, the beads were further washed five times with the wash buffer and then transferred to qPCR plate for SYBR® qPCR. 25 uL per well of SYBR® qPCR reaction was set up using Takara's SYBR® qPCR kit. For control reactions, serial dilutions of the nucleic acid molecule including the surrogate nucleic acid were run directly in SYBR® qPCR.

PCR reaction mixture contained:

| Reagents | Volume | Final Concentration |
| --- | --- | --- |
| SYBR ® Premix Ex Taq ™ | 12.5 uL | 1x |
| PCR forward primer (10 uM) | 0.5 uL | 0.2 uM |
| PCR reverse primer (10 uM) | 0.5 uL | 0.2 uM |
| ROX ™ Reference Dye II (50x) | 0.5 uL | 1x |

-continued

| Reagents | Volume | Final Concentration |
|---|---|---|
| Bead-associated surrogate amplicon | 2 uL | |
| dH2O | 9 uL | |
| Total | 25 uL. | |

PCR conditions using Stratagene's Mx4000® qPCR system were:

Segment 1: Initial denaturation
  Repetitions: 1
  95° C. 10 sec
Segment 2: PCR
  Repetitions: 40
  95° C. 5 sec
  60° C. 20 sec Results of the sqPCR, in which the surrogate nucleic acid was captured to the IL-6 target and then amplified and detected, are shown in FIG. 4 Panel B (diamonds). Results from control amplifications of the surrogate nucleic acid (i.e., dilutions of the surrogate nucleic acid, not captured to the target) are also shown (squares). The surrogate qPCR experiment successfully detected the IL-6 target and permitted its quantitation even at amounts as low as 0.004 amol (2500 molecules).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising:
    a first target nucleic acid;
    a nucleic acid comprising a first surrogate nucleic acid;
    a first set of two or more surrogate capture probes, each of which surrogate capture probes is capable of hybridizing simultaneously to the first target nucleic acid and to the nucleic acid comprising the first surrogate nucleic acid, wherein the 5' end of each of the surrogate capture probes in the first set hybridizes to the first target nucleic acid while the 3' end hybridizes to the nucleic acid comprising the first surrogate nucleic acid, or wherein the 3' end of each of the surrogate capture probes in the first set hybridizes to the first target nucleic acid while the 5' end hybridizes to the nucleic acid comprising the first surrogate nucleic acid;
    a solid support;
    a first set of m target capture probes, where m is at least one, which target capture probes are capable of hybridizing to the first target nucleic acid; and
    one or more primers for amplifying the first surrogate nucleic acid.

2. The composition of claim 1, wherein the nucleic acid comprising the first surrogate nucleic acid is hybridized to the first set of surrogate capture probes, which surrogate capture probes are hybridized to the first target nucleic acid, whereby the first surrogate nucleic acid is physically associated with the first target nucleic acid at a molar ratio of about 1:1.

3. The composition of claim 1, wherein the nucleic acid comprising the first surrogate nucleic acid is hybridized to the first set of surrogate capture probes, which surrogate capture probes are hybridized to the first target nucleic acid, whereby the first surrogate nucleic acid is physically associated with the first target nucleic acid at a molar ratio of at least about 2:1, at least about 3:1, at least about 5:1, or at least about 10:1 first surrogate nucleic acid:first target nucleic acid.

4. The composition of claim 1, wherein one or more copies of the nucleic acid comprising the first surrogate nucleic acid are associated with a copy of the first target nucleic acid; wherein the first set of surrogate capture probes comprises a subset of surrogate capture probes for each of the one or more copies of the nucleic acid comprising the first surrogate nucleic acid; and wherein each subset of surrogate capture probes comprises n surrogate capture probes, where n is at least two.

5. The composition of claim 1, wherein the surrogate capture probes hybridize to nonoverlapping polynucleotide sequences in the first target nucleic acid.

6. The composition of claim 1, wherein the solid support comprises a plurality of particles.

7. The composition of claim 1, wherein the target capture probes hybridize to nonoverlapping polynucleotide sequences in the first target nucleic acid.

8. The composition of claim 1, wherein m is at least two.

9. The composition of claim 1, wherein the solid support comprises a first support capture probe bound to the solid support, and wherein the target capture probes of the first set are capable of hybridizing simultaneously to the first target nucleic acid and to the first support capture probe.

10. The composition of claim 1, comprising amplified first surrogate nucleic acid.

11. The composition of claim 10, comprising one or more reagents for detecting the amplified first surrogate nucleic acid.

12. The composition of claim 1, wherein the first surrogate nucleic acid is a DNA.

13. The composition of claim 1, comprising a second nucleic acid comprising a second surrogate nucleic acid; a second set of one or more surrogate capture probes, each of which surrogate capture probes is capable of hybridizing simultaneously to a second target nucleic acid and to the second nucleic acid comprising the second surrogate nucleic acid; and the second target nucleic acid and/or one or more primers for amplifying the second surrogate nucleic acid.

14. A kit comprising:
a nucleic acid comprising a first surrogate nucleic acid;
a first set of two or more surrogate capture probes, each of which surrogate capture probes is capable of hybridizing simultaneously to a first target nucleic acid and to the nucleic acid comprising the first surrogate nucleic acid, wherein the 5' end of each of the surrogate capture probes in the first set hybridizes to the first target nucleic acid while the 3' end hybridizes to the nucleic acid comprising the first surrogate nucleic acid, or wherein the 3' end of each of the surrogate capture probes in the first set hybridizes to the first target nucleic acid while the 5' end hybridizes to the nucleic acid comprising the first surrogate nucleic acid;
a solid support comprising a first support capture probe bound to the solid support;
a first set of m target capture probes, where m is at least one, which target capture probes are capable of hybridizing simultaneously to the first target nucleic acid and to the first support capture probe; and
one or more primers for amplifying the first surrogate nucleic acid;
packaged in one or more containers.

15. The kit of claim 14, further comprising:
a second nucleic acid comprising a second surrogate nucleic acid;
a second set of one or more surrogate capture probes, each of which surrogate capture probes is capable of hybridizing simultaneously to a second target nucleic acid and to the second nucleic acid comprising the second surrogate nucleic acid; and
a second set of m target capture probes, where m is at least one, which target capture probes are capable of hybridizing simultaneously to the second target nucleic acid and to the first support capture probe.

16. The composition of claim 1, wherein the first surrogate nucleic acid is physically associated with the first target nucleic acid.

* * * * *